US006790622B2

(12) United States Patent
Kwok et al.

(10) Patent No.: US 6,790,622 B2
(45) Date of Patent: Sep. 14, 2004

(54) TUMOR SUPPRESSOR ENCODING NUCLEIC ACID, PTX1, AND METHODS OF USE THEREOF

(75) Inventors: Simon Kwok, Devon, PA (US); Ierachimiel Daskal, Elkins Park, PA (US)

(73) Assignee: Albert Einstein Healthcare Network, Philadelphia, PA (US)

( * ) Notice: Subject to any disclaimer, the term of this patent is extended or adjusted under 35 U.S.C. 154(b) by 39 days.

(21) Appl. No.: 10/094,474

(22) Filed: Mar. 8, 2002

(65) Prior Publication Data

US 2002/0132262 A1 Sep. 19, 2002

Related U.S. Application Data

(62) Division of application No. 09/935,038, filed on Aug. 22, 2001
(60) Provisional application No. 60/226,993, filed on Aug. 22, 2000.

(51) Int. Cl.[7] ............................ C12Q 1/68; C07H 21/04
(52) U.S. Cl. ............................ 435/6; 436/64; 536/24.31
(58) Field of Search .......................... 435/6; 536/24.31; 436/64

(56) References Cited

FOREIGN PATENT DOCUMENTS

WO    WO 98/25959    *    6/1998

OTHER PUBLICATIONS

Salomon et al (Urology, Aug. 2003, 62(2): 304–9 abstract only).*

Kwok, Simon C.M. et al.; "Molecular Cloning, Expression, Localization, and Gene Organization of PTX1, a Human Nuclear Protein That Is Downregulated in Prostate Cancer"; DNA and Cell Biology, 20(6): 349–357 (2001).

Luu, Hue H. et al., "Identification of a Novel Metastasis–suppressor Region on Human Chromosome 12"; Cancer Research, 58: 3561–3565 (1998).

Kibel, Adam S., "Identification of 12p as a Region of Frequent Deletion in Advanced Prostate Cancer"; Cancer Research, 58: 5652–5655 (1998).

Berube, Nathalie G. et al., "Suppression of Tumorigenicity of Human Prostate Cancer Cells by Introduction of Human Chromosome del(12)(q13)"; Cancer Research, 54: 3077–3081 (1994).

Song, H. et al., "A novel gene expressed in human pheochromocytoma"; Chinese National Human Genome Center (1999) [Abstract].

Song, H. et al., "A novel gene expressed in human pheochromocytoma"; Gen Bank Accession No.: AF216751.

Song, H. et al., "A novel gene expressed in human pheochromocytoma"; Gen Bank Accession No.: NM_016570.

* cited by examiner

Primary Examiner—Larry R. Helms
Assistant Examiner—Misook Yu
(74) Attorney, Agent, or Firm—Dann, Dorfman, Herrell and Skillman

(57) ABSTRACT

This invention provides a novel nucleic acid molecule encoding PTX1, which has been mapped to human chromosome 12. The PTX1-encoding nucleic acid molecule, along with its encoded protein and antibodies thereto may be used to advantage to facilitate the diagnosis, prognosis and treatment of cancer.

5 Claims, 9 Drawing Sheets

Figure 2

```
                                                               GACCCGGGCTTCTGT    15
GAAACATGGCGGTAGGCTGGGACCATAACACAAGCATGACTATATGAAGGAAGAGGAAGGTTTTCCTGAAG            86

ATG AGG CGA CTG AAT CGG AAA AAA ACT TTA AGT TTG GTA AAA GAG TTG GAT GCC          140
 M   R   R   L   N   R   K   K   T   L   S   L   V   K   E   L   D   A           18

TTT CCG AAG GTT CCT GAG AGC TAT GTA GAG ACT TCA GCC AGT GGA GGT ACA GTT          194
 F   P   K   V   P   E   S   Y   V   E   T   S   A   S   G   G   T   V           36

TCT CTA ATA GCA TTT ACA ACT ATG GCT TTA TTA ACC ATA ATG AAA TTC TCA GTA          248
 S   L   I   A   F   T   T   M   A   L   L   T   I   M   K   F   S   V           54

TAT CAA GAT ACA TGG ATG AAG TAT GAA TAC GAA GTA GAC AAG GAT TTT TCT AGC          302
 Y   Q   D   T   W   M   K   Y   E   Y   E   V   D   K   D   F   S   S           72

AAA TTA AGA ATT AAT ATA GAT ATT ACT GTT GCC ATG AAG TGT CAA TAT GTT GGA          356
 K   L   R   I   N   I   D   I   T   V   A   M   K   C   Q   Y   V   G           90

GCG GAT GTA TTG GAT TTA GCA GAA ACA ATG GTT GCA TCT GCA GAT GGT TTA GTT          410
 A   D   V   L   D   L   A   E   T   M   V   A   S   A   D   G   L   V          108

TAT GAA CCA ACA GTA TTT GAT CTT TCA CCA CAG CAG AAA GAG TGG CAG AGG ATG          464
 Y   E   P   T   V   F   D   L   S   P   Q   Q   K   E   W   Q   R   M          126

CTG CAG CTG ATT CAG AGT AGG CTA CAA GAA GAG CAT TCA CTT CAA GAT GTG ATA          518
 L   Q   L   I   Q   S   R   L   Q   E   E   H   S   L   Q   D   V   I          144

TTT AAA AGT GCT TTT AAA AGT ACA TCA ACA GCT CTT CCA CCA AGA GAA GAT GAT          572
 F   K   S   A   F   K   S   T   S   T   A   L   P   P   R   E   D   D          162

TCA TCA CAG TCT CCA AAT GCA TGC AGA ATT CAT GGC CAT CTA TAT GTC AAT AAA          626
 S   S   Q   S   P   N   A   C   R   I   H   G   H   L   Y   V   N   K          180

GTA GCA GGG AAT TTT CAC ATA ACA GTG GGC AAG GCA ATT CCA CAT CCT CGT GGT          680
 V   A   G   N   F   H   I   T   V   G   K   A   I   P   H   P   R   G          198

CAT GCA CAT TTG GCA GCA CTT GTC AAC CAT GAA TCT TAC AAT TTT TCT CAT AGA          734
 H   A   H   L   A   A   L   V   N   H   E   S   Y   N   F   S   H   R          216

ATA GAT CAT TTG TCT TTT GGA GAG CTT GTT CCA GCA ATT ATT AAT CCT TTA GAT          788
 I   D   H   L   S   F   G   E   L   V   P   A   I   I   N   P   L   D          234

GGA ACT GAA AAA ATT GCT ATA GAT CAC AAC CAG ATG TTC CAA TAT TTT ATT ACA          842
 G   T   E   K   I   A   I   D   H   N   Q   M   F   Q   Y   F   I   T          252

GTT GTG CCA ACA AAA CTA CAT ACA TAT AAA ATA TCA GCA TAC ACC CAT CAG TTT          896
 V   V   P   T   K   L   H   T   Y   K   I   S   A   Y   T   H   Q   F          270

TCT GTG ACA GAA AGG GAA CGT ATC ATT AAC CAT GCT GCA GGC AGC CAT GGA GTC          950
 S   V   T   E   R   E   R   I   I   N   H   A   A   G   S   H   G   V          288

TCT GGG ATA TTT ATG AAA TAT GAT CTC AGT TCT CTT ATG GTG ACA GTT ACT GAG         1004
 S   G   I   F   M   K   Y   D   L   S   S   L   M   V   T   V   T   E          306

GAG CAC ATG CCA TTC TGG CAG TTT TTT GTA AGA CTC TGT GGT ATT GTT GGA GGA         1058
 E   H   M   P   F   W   Q   F   F   V   R   L   C   G   I   V   G   G          324

ATC TTT TCA ACA ACA GGC ATG TTA CAT GGA ATT GGA AAA TTT ATA GTT GAA ATA         1112
 I   F   S   T   T   G   M   L   H   G   I   G   K   F   I   V   E   I          342

ATT TGC TGT CGT TTC AGA CTT GGA TCC TAT AAA CCT GTC AAT TCT GTT CCT TTT         1166
 I   C   C   R   F   R   L   G   S   Y   K   P   V   N   S   V   P   F          360

GAG GAT GGC CAC ACA GAC AAC CAC TTA CCT CTT TTA GAA AAT AAT ACA CAT TAA         1220
 E   D   G   H   T   D   N   H   L   P   L   L   E   N   N   T   H   *          377

CACCTCCCGATTGAAGGAGAAAAACTTTTTGCCTGAGACATAAAACCTTTTTTTAATAATAAAATATTGTG         1291
CAATATATCCAAAAAAAAAAAAAAAAAAAAAAAAAAA                                           1327
```

```
  1  MRRLNRKKTLSLVKELDAFPKVPESYVETSASGGTVSLIAFTTMALLTIM   50
     ||||||||||||||||||||||||||||||||||||||||||||||||||
  1  MRRLNRKKTLSLVKELDAFPKVPESYVETSASGGTVSLIAFTTMALLTIM   50

51  KFSVYQDTWMKYEYEVDKDFSSKLRINIDITVAMKCQYVGADVLDLAETM  100
     |||||||||||||||||||||||||||||||||||||||||||||||||
 51  EFSVYQDTWMKYEYEVDKDFSSKLRINIDITVAMKCQYVGADVLDLAETM  100

101  VASADGLVYEPTVFDLSPQQKEWQRMLQLIQSRLQEEHSLQDVIFKSAFK  150
     |||||||||||||||||||||||||||||||||||||||||||||||||
101  VASADGLVYEPTVFDLSPQQKEWQRMLQLIQSRLQEEHSLQDVIFKSAFK  150

151  STSTALPPREDDSSQSPNACRIHGHLYVNKVAGNFHITVGKAIPHPRGHA  200
     |||||||||||||||||||||||||||||||||||||||||||||||||
151  STSTALPPREDDSSQSPNACRIHGHLYVNKVAGNFHITVGKAIPHPRGHA  200

201  HLAALVNHESY----N---FSHRIDHLSFGELVPAIINPLDGTEKIAIDH  243
     ||         |    |  ||||||||||||||||||||||||||||||
201  HLG------STCQPWNLTIFSHRIDHLSFGELVPAIINPLDGTEKIAIDH  244

244  NQMFQYFITVVPTKLHTYKISAYTHQFSVTERERIINHAAGSHGVSGIFM  293
     ||||||||||||||||||||||| ||||||||||||||||||||||||||
245  NQMFQYFITVVPTKLHTYKISADTHQFSVTERERIINHAAGSHGVSGIFM  294

294  KYDLSSLMVTVTEEHMPFWQFFVRLCGIVGGIFSTTGMLHGIGKFIVEII  343
     |||||||||||||||||||||||||||||||||||||||||||||||||
295  KYDLSSLMVTVTEEHMPFWQFFVRLCGIVGGIFSTTGMLHGIGKFIVEII  344

344  CCRFRLGSYKPVNSVPFEDGHTDNHLPLLENNTH                  377
     ||||||||||||||||||||||||||||||||||
345  CCRFRLGSYKPVNSVPFEDGHTDNHLPLLENNTH                  378
```

Figure 9

| Exon # | Size (bp) | Intron # | Size (kb) | 5' Splice Junctions | 3' Splice Junction | Codon(s) Interrupted |
|---|---|---|---|---|---|---|
| 1 | 49 | | | | | |
| | | 1 | 9.4 | 158697<br>CATAACACAAG gtaaaatactga | 149252<br>tttattccttag CATGACTATAT | |
| 2 | 143 | | | | | |
| | | 2 | 1.3 | 149110<br>GGT ACA G gtgagtatcagt | 147804<br>tggattcccag TT TCT CTA | $V^{36}$ |
| 3 | 109 | | | | | |
| | | 3 | 1.8 | 147696<br>TTT TCT AG gtaatcattttt | 145869<br>tttgtctttcag C AAA TTA | $S^{72}$ |
| 4 | 47 | | | | | |
| | | 4 | 1.3 | 145823<br>TGT CAA T gtaagtacacct | 144529<br>ttctctatgcag AT GTT GGA | $Y^{88}$ |
| 5 | 71 | | | | | |
| | | 5 | 5.2 | 144459<br>TAT GAA CCA gtaagtttgatt | 139267<br>ctttccattcag ACA GTA TTT | $P^{111}/T^{112}$ |
| 6 | 41 | | | | | |
| | | 6 | 3.9 | 139227<br>TGG CAG AG gtaataagagaa | 135306<br>cttctatttag G ATG CTG | $R^{125}$ |
| 7 | 102 | | | | | |
| | | 7 | 1.1 | 135205<br>CCA CCA AG gtgagatctgta | 134059<br>ttatttaacag A GAA GAT | $R^{159}$ |
| 8 | 96 | | | | | |
| | | 8 | 6.3 | 133964<br>GTG GGC AA gtatgttctttt | 127650<br>ttctcctttcag G GCA ATT | $K^{191}$ |
| 9 | 56 | | | | | |
| | | 9 | 0.8 | 127595<br>CAT GAA T gtaagcagattc | 126759<br>tttgcctttag CT TAC AAT | $S^{210}$ |
| 10 | 99 | | | | | |
| | | 10 | 3.5 | 126661<br>ATA GAT C gtaagtatttaa | 123122<br>tttgtattctag AC AAC CAG | $H^{241}$ |
| 11 | 98 | | | | | |
| | | 11 | 2.2 | 123025<br>ACA GAA AGG gtaagttgaatc | 120864<br>cctccctttag GAA CGT ATC | $R^{275}/E^{276}$ |
| 12 | 163 | | | | | |
| | | 12 | 1.3 | 120702<br>ACA ACA G gttaacaaccat | 119398<br>tgtttattacag GC ATG TTA | $G^{330}$ |
| 13 | 83 | | | | | |
| | | 13 | 0.5 | 119316<br>GTC ATT TCT gtaagtggtgta | 118800<br>ttttctccttag GTT CCT TTT | $S^{357}/V^{358}$ |
| 14 | 140 | | | | | |

US 6,790,622 B2

TUMOR SUPPRESSOR ENCODING NUCLEIC ACID, PTX1, AND METHODS OF USE THEREOF

The present application is a Divisional Application of U.S. patent application Ser. No. 09/935,038, filed Aug. 22, 2001 which in turn claims priority under 35 U.S.C. §119(e) to U.S. Provisional Application 60/226,993, filed Aug. 22, 2000, the entire disclosures of which are incorporated by reference herein.

FIELD OF THE INVENTION

The present invention relates to the diagnosis and treatment of prostate cancer, and more specifically, to novel nucleic acid molecules, proteins and antibodies immunologically specific therefore which may be used to advantage for the diagnosis and treatment of prostate cancer.

BACKGROUND OF THE INVENTION

Several publications are referenced in this application by author name and year of publication in parentheses in order to more fully describe the state of the art to which this invention pertains. The disclosure of each of these publications is incorporated by reference herein.

The molecular basis of cancer has been the subject of a massive research effort over the past several years. Through this effort, it has been discovered that abnormal cellular proliferation results not only from activation of oncogenes, but from disruption of certain genes whose function appears to be important in maintaining normal cell division. As a well-known example, mutations in the p53 tumor suppressor gene are common in human cancer and have been detected in tumor types from many different tissue sources.

This year prostate cancer is expected to be diagnosed in approximately 200,000 men in the U.S. and to result in the loss of 38,000 lives. Such numbers make prostate cancer the most frequently diagnosed malignancy (other than that of the skin) in American males and the second leading cause of cancer-related death in that group. Physicians usually detect cancers by finding a lump in the prostate gland, which is a walnut shaped structure that helps to maintain the viability of sperm. Such lumps may be discovered during a routine checkup or during examinations prompted by a patient's complaint of sudden urinary discomfort or occasional impotence.

In some instances, prostate cancer is detected in the course of treatment for a disorder called benign prostatic hyperplasia. This condition, an aging-related enlargement of the prostate, affects more than half of all men older than 45 and gives rise (albeit more gradually) to the same urinary troubles caused by a prostate tumor. If the symptoms become too troublesome, a transurethral resection of the prostate, a process whereby parts of the gland are scraped away, may be performed. Whenever resection is done, the excised tissue is analyzed under a microscope for evidence of malignancy, which is occasionally found.

A simple blood test for prostate specific antigen (PSA) constitutes a third means of detecting prostate cancer. Increased PSA levels can signal the presence of cancer in individuals who display no symptoms of prostate abnormalities.

Prostate cancer is a disease with marked heterogeneity. Although many genes have been identified which are associated with the carcinogenesis of the prostate (Lara et al., 1999; Sciavolino and Abate-Shen, 1998), the mechanism underlying the development of prostate cancer is still poorly understood. However, it is believed to be a multi-step process that involves genetic alterations of genes controlling cellular proliferation, differentiation and programmed cell death. Deletion or down-regulation of these tumor suppressor genes often leads to the development of cancer.

SUMMARY OF THE INVENTION

To further understand the biological processes underlying the development of prostate cancer, the present inventors have identified a tumor suppressor gene which is expressed in normal but not malignant prostate tissue. Thus, in accordance with the present invention, novel biological molecules useful for identification, detection, and/or molecular characterization of components involved in the regulation of cellular differentiation and tumorigenesis are provided.

In a preferred embodiment of the invention, an isolated nucleic acid molecule is provided which encodes the human PTX1 protein. In a particularly preferred embodiment, the human PTX1 protein has an amino acid sequence comprising the sequence of SEQ ID NO:2. An exemplary PTX1 nucleic acid molecule of the invention comprises the sequence of SEQ ID NO:1.

According to another aspect of the present invention, an isolated nucleic acid molecule is provided, which has a sequence selected from the group consisting of: (1) SEQ ID NO: 1; (2) a sequence specifically hybridizing with preselected portions or all of the complementary strand of SEQ ID NO: 1; (3) a sequence comprising preselected portions of SEQ ID NO:1, (4) a complement of SEQ ID NO: 1, and (5) a sequence encoding part or all of a polypeptide comprising the sequence of SEQ ID NO: 2. Such partial sequences are useful as probes to identify and isolate homologues of the PTX1 gene of the invention. Accordingly, isolated nucleic acid sequences encoding natural allelic variants of the nucleic acids of SEQ ID NO: 1 are also contemplated to be within the scope of the present invention. The term natural allelic variants will be defined hereinbelow.

Host cells comprising the PTX1-encoding nucleic acids of the invention are also contemplated to be within the scope of the present invention. Such host cells include but are not limited to bacterial cells, fungal cells, yeast cells, plant cells, insect cells and other animal cells. The PTX1-encoding nucleic acids may be conveniently cloned into a plasmid or retroviral vector for introduction into host cells. Such cells are useful in screening methods to identify compounds which modulate PTX1 expression. Compounds so identified may have therapeutic value in the treatment of prostate cancer.

According to another aspect of the present invention, an isolated human PTX1 protein is provided. The loss of expression of this PTX1 protein correlates with the deregulated growth of prostate carcinomas.

In a preferred embodiment of the invention, the protein is of human origin, and comprises the amino acid sequence of SEQ ID NO: 2. In a further embodiment, the protein may be encoded by natural allelic variants of SEQ ID NO: 1. Inasmuch as certain amino acid variations may be present in human PTX1 protein encoded by natural allelic variants, such proteins are also contemplated to be within the scope of the invention. Antibodies immunologically specific for the human PTX1 protein described hereinabove are also provided.

In yet another aspect of the invention, methods are provided for genetic screening and diagnostic evaluation of patients at risk for, or currently suffering from, cancer of the prostate. The hybridization specificity of the nucleic acids of the invention may be used to advantage for differential evaluation of patients presenting with phenotypic characteristics common to prostate cancer. In a preferred embodiment of the invention, a method for identifying a mutation in a nucleic acid sequence in a patient sample is provided. This method comprises isolating a nucleic acid sample from a patient, contacting the nucleic acid sample with a nucleic acid sequence of SEQ ID NO: 1 under low stringency hybridization conditions to allow DNA duplexes to form between sequences of sufficient complementarity, isolating the DNA duplexes and assessing the duplexes for mismatched base pairing.

In another embodiment, the nucleic acid molecules of the invention may be used as diagnostic hybridization probes or as primers for diagnostic PCR analysis for PTX1 or mutations thereof. Antisense molecules are also provided herein and may be useful in the regulation of PTX1 expression. Other methods encompassed by the present invention include immunodetection methods for assessing biological samples for the presence of PTX1 proteins.

According to another aspect of the invention, a method is provided for identifying agents which modulate PTX1 activity. This method comprises contacting cells expressing PTX1 with an agent suspected of being able to modulate PTX1 activity, measuring proliferation of the cells expressing PTX1 in both the presence and absence of the agent and comparing the proliferation of cells expressing PTX1 in the absence of the agent and in the presence of the agent. An alteration in cell proliferation in the presence of the agent is indicative of the agent's ability to modulate PTX1 activity.

In yet another embodiment of the invention, kits are provided for detecting PTX1 expression associated with a susceptibility to cancer. Such kits may be used to advantage to diagnose human prostate cancer.

BRIEF DESCRIPTION OF THE DRAWINGS

FIG. 2 shows the nucleotide sequence of the full-length PTX1 cDNA (SEQ ID NO: 1). The composite nucleotide sequence of overlapping cDNAs and its translation into the PTX1 protein are presented in the 5' to 3' direction. The numbering of the nucleotide and amino acid sequences (SEQ ID NO: 2) are shown at the right-hand side. The AATAAA sequence is underlined.

FIG. 6 shows a comparison of nucleotide sequences of PTX1 and CDA14 cDNAs (SEQ ID NOS: 1 and 4, respectively). Alignment was based on the nucleotide sequences of PTX1 (top, this study) and published sequence of CDA14 (bottom, Song et al., 2000). Gaps were introduced where necessary to maximize the alignment. The vertical line indicates identical nucleotides. Please note the five single base differences in the coding sequence.

FIG. 7 shows the alignment of the deduced amino acid sequences of PTX1 and CDA14 proteins. The amino acid sequence of PTX1 (top; SEQ ID NO: 2) and CDA14 (bottom; SEQ ID NO: 5) were aligned with gaps introduced where necessary to maximize the homology. The vertical line indicates identical residues. Please note the altered reading frame caused by three single base insertions.

FIG. 9 shows the exon-intron junctions of the human PTX1 gene as determined from the genomic sequence deposited under accession number AC009318 (Muzny et al., 2000). The sequences of the exon-intron junctions shown here are complementary to the published genomic sequence (SEQ ID NOS: 6–31). Exon sequences are in capital letters; while intron sequences are in lower case letters. The number shown on top of the exon sequences denotes the boundaries of the exons on the genomic sequence.

DETAILED DESCRIPTION OF THE INVENTION

Figure 1:
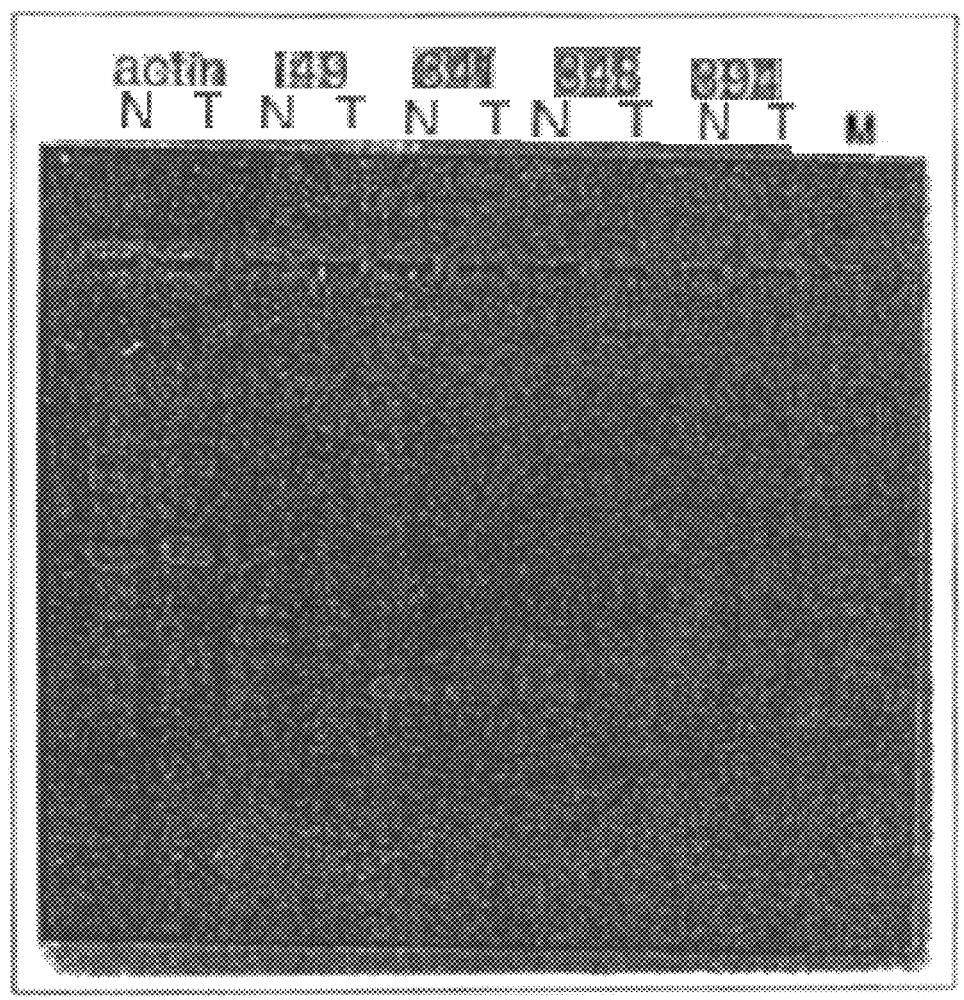
FIG. 1 is a gel showing the differential expression of four selected clones by RT-PCR. First strand cDNAs were synthesized from 10 μg of total RNA isolated from normal prostate (N) and prostate tumor (T). Aliquots of 2 μl of the cDNA were amplified using primers specific to each clone. The PCR products were analyzed on 2% agarose gel. Molecular size marker (M) was pBR322 DNA digested with Bst N I. Clones 149 and 348 were expressed only in normal prostate, as indicated by the presence of a band in normal prostate (N), but not in prostate tumor (T). Clones 341 and 394 were expressed by both normal prostate and prostate tumor. Clone 348 was selected for further characterization and has been designated PTX1 herein.

In accordance with the present invention, a new gene from human chromosome 12, designated PTX1, has been isolated by subtractive hybridization. PTX1, which is expressed in normal but not prostate tumor tissue, plays a role in suppression of prostate tumor development.

The full-length cDNA encoding PTX1 was isolated by 5'- and 3'-RACE. Nucleotide sequence analysis of the 1327-bp cDNA (SEQ ID NO: 1) predicts a protein of 377 amino acid residues (SEQ ID NO: 2) with a putative nuclear import signal (RRLNRKK; SEQ ID NO: 3) at its amino-terminus.

The PTX1 gene is localized on human chromosome 12 and is ubiquitously expressed. A segment of the cDNA was expressed in E. coli to produce a fragment of the PTX1 protein for the production of specific antibodies. Using immunohistochemical analysis, PTX1 protein was localized to the nuclei of glandular epithelia (especially in basal cells) of normal prostate but not in prostate carcinoma. The gene organization of PTX1 was established by comparing the cDNA sequence with a published human genomic sequence of unknown function.

The composition of the invention may be used to advantage in the diagnosis and treatment of prostate cancer. The nucleic acids of the invention may be used in chromosome and gene mapping assays for PCR; for the production of sense and antisense nucleic acids for altering gene expression levels; and/or for the production of peptide fragments and for the production of immunospecific antibodies. Methods are also provided for assessing genetic and biochemical alterations in PTX1 activity as well as the identification of agents capable of altering PTX1 activity. Such agents may be used to advantage as therapeutic agents for the treatment of prostate cancer. Finally, PTX1 gene replacement therapies are also within the scope of the present invention.

I. Definitions

The following definitions are provided to facilitate an understanding of the present invention:

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

"Natural allelic variants", "mutants" and "derivatives" of particular sequences of nucleic acids refer to nucleic acid sequences that are closely related to a particular sequence but which may possess, either naturally or by design, changes in sequence or structure. By closely related, it is meant that at least about 75%, but often, more than 90%, of the nucleotides of the sequence match over the defined length of the nucleic acid sequence referred to using a specific sequence identification number (SEQ ID NO).

Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to change an amino acid codon or sequence in a regulatory region of the nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence.

The terms "percent similarity", "percent identity" and "percent homology" when referring to a particular sequence are used as set forth in the University of Wisconsin GCG software program.

The present invention also includes active portions, fragments, derivatives and functional or non-functional mimetics of PTX1 polypeptides, or proteins of the invention. An "active portion" of such a polypeptide means a peptide that is less than the full length polypeptide, but which retains measurable biological activity.

A "fragment" or "portion" of a PTX1 polypeptide means a stretch of amino acid residues of at least about five to seven contiguous amino acids, often at least about seven to nine contiguous amino acids, typically at least about nine to thirteen contiguous amino acids and, most preferably, at least about twenty to thirty or more contiguous amino acids. Fragments of the PTX1 polypeptide sequence, antigenic determinants, or epitopes are useful for eliciting immune responses to a portion of the PTX1 protein amino acid sequence.

Different "variants" of the PTX1 polypeptides exist in nature. These variants may be alleles characterized by differences in the nucleotide sequences of the gene coding for the protein, or may involve different RNA processing or post-translational modifications. The skilled person can produce variants having single or multiple amino acid substitutions, deletions, additions or replacements. These variants may include inter alia: (a) variants in which one or more amino acids residues are substituted with conservative or non-conservative amino acids, (b) variants in which one or more amino acids are added to the polypeptide, (c) variants in which one or more amino acids include a substituent group, and (d) variants in which the polypeptide is fused with another peptide or polypeptide such as a fusion partner, a protein tag or other chemical moiety, that may confer useful properties to the PTX1 polypeptide, such as, for example, an epitope for an antibody, a polyhistidine sequence, a biotin moiety and the like. Other PTX1 polypeptides of the invention include variants in which amino acid residues from one species are substituted for the corresponding residue in another species, either at the conserved or non-conserved positions. In another embodiment, amino acid residues at non-conserved positions are substituted with conservative or non-conservative residues. The techniques for obtaining these variants, including genetic (suppressions, deletions, mutations, etc.), chemical, and enzymatic techniques are known to the person having ordinary skill in the art. To the extent such allelic variations, analogues, fragments, derivatives, mutants, and modifications, including alternative nucleic acid processing forms and alternative post-translational modification forms, result in derivatives of the PTX1 polypeptide that retain any of the biological properties of the PTX1 polypeptide, they are included within the scope of this invention.

The term "functional" as used herein implies that the nucleic or amino acid sequence is functional for the recited assay or purpose.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the basic and novel characteristics of the sequence.

A "replicon" is any genetic element, for example, a plasmid, cosmid, bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "oligonucleotide," as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, for diagnostic applications, depending on the complexity of the target sequence, the oligonucleotide probe typically contains 15-25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as appropriate temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15–25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The terms "transform", "transfect", "transducer", shall refer to any method or means by which a nucleic acid is introduced into a cell or host organism and may be used interchangeably to convey the same meaning. Such methods include, but are not limited to, transfection, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

Amino acid residues are identified in the present application according to the three-letter or one-letter abbreviations in the following Table:

TABLE I

| Amino Acid | 3-letter Abbreviation | 1-letter Abbreviation |
| --- | --- | --- |
| L-Alanine | Ala | A |
| L-Arginine | Arg | R |
| L-Asparagine | Asn | N |
| L-Aspartic Acid | Asp | D |
| L-Cysteine | Cys | C |
| L-Glutamine | Gln | Q |
| L-Glutamic Acid | Glu | E |
| Glycine | Gly | G |
| L-Histidine | His | H |
| L-Isoleucine | Ile | I |
| L-Leucine | Leu | L |
| L-Methionine | Met | M |
| L-Phenylalanine | Phe | F |
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |
| L-Lysine | Lys | K |

Amino acid residues described herein are preferred to be in the "L" isomeric form. However, residues in the "D" isomeric form may be substituted for any L-amino acid residue, provided the desired properties of the polypeptide are retained. All amino-acid residue sequences represented herein conform to the conventional left-to-right amino-terminus to carboxy-terminus orientation.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

The term "substantially pure" refers to a preparation comprising at least 50–60% by weight of a given material (e.g., nucleic acid, oligonucleotide, protein, etc.). More preferably, the preparation comprises at least 75% by weight, and most preferably 90–95% by weight of the given compound. Purity is measured by methods appropriate for the given compound (e.g. chromatographic methods, agarose or polyacrylamide gel electrophoresis, HPLC analysis, and the like).

"Mature protein" or "mature polypeptide" shall mean a polypeptide possessing the sequence of the polypeptide after any processing events that normally occur to the polypeptide during the course of its genesis, such as protoelytic processing from a polyprotein precursor. In designating the sequence or boundaries of a mature protein, the first amino of the mature protein sequence is designated as amino acid residue 1. As used herein, any amino acid residues associated with a mature protein not naturally found associated with that protein that precedes amino acid 1 are designated amino acid −1, −2, −3 and so on. For recombinant expression systems, a methionine initiator codon is often utilized for purposes of efficient translation. This methionine residue in the resulting polypeptide, as used herein, would be positioned at −1 relative to the mature PTX1 protein sequence.

The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, of that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins to facilitate isolation or detection by interaction with avidin reagents, and the like. Numerous other tag moieties are known to, and can be envisioned by the trained artisan, and are contemplated to be within the scope of this definition.

A "clone" or "clonal cell population" is a population of cells derived from a single cell or common ancestor by mitosis.

A "cell line" is a clone of a primary cell or cell population that is capable of stable growth in vitro for many generations.

An "immune response" signifies any reaction produced by an antigen, such as a viral antigen, in a host having a functioning immune system. Immune responses may be either humoral in nature, that is, involve production of immunoglobulins or antibodies, or cellular in nature, involving various types of B and T lymphocytes, dendritic cells, macrophages, antigen presenting cells and the like, or both. Immune responses may also involve the production or elaboration of various effector molecules such as cytokines, lymphokines and the like. Immune responses may be measured both in in vitro and in various cellular or animal systems. Such immune responses may be important in protecting the host from disease and may be used prophylactically and therapeutically.

An "antibody" or "antibody molecule" is any immunoglobulin, including antibodies and fragments thereof, that binds to a specific antigen. The term includes polyclonal, monoclonal, chimeric, and bispecific antibodies.

As used herein, antibody or antibody molecule contemplates both an intact immunoglobulin molecule and an immunologically active portion of an immunoglobulin molecule such as those portions known in the art as Fab, Fab', F(ab')2 and F(v).

As used herein, the term "living host" shall mean any non-human autonomous being.

II. Preparation of PTX1-Encoding Nucleic Acid Molecules, PTX1 Proteins, and Antibodies Thereto A. Nucleic Acid Molecules Nucleic acid molecules encoding the PTX1 proteins of the invention may be prepared by two general methods: (1) They may be synthesized from appropriate nucleotide triphosphates, or (2) they may be obtained from biological sources. Both methods utilize protocols well known in the art.

The availability of nucleotide sequence information, such as the full length cDNA having SEQ ID NO: 1, enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a 2.6 kb double-stranded molecule may be synthesized as several smaller segments of appropriate complementarity. Complementary segments produced may then be annealed such that each segment possesses appropriate cohesive termini for attachment of an adjacent segment. Adjacent segments may be ligated by annealing cohesive termini in the presence of DNA ligase to construct an entire 2.6 kb double-stranded molecule. A synthetic DNA molecule so constructed may then be cloned and amplified in an appropriate vector.

Nucleic acid sequences encoding PTX1 may be isolated from appropriate biological sources using methods known in the art. In a preferred embodiment, a cDNA clone is isolated from an expression library of human origin. In an alternative embodiment, genomic clones encoding PTX1 may be isolated. Alternatively, cDNA or genomic clones encoding PTX1 from other animal species may be obtained.

In accordance with the present invention, nucleic acids having the appropriate level of sequence homology with the protein coding region of SEQ ID NO: 1 may be identified by using hybridization and washing conditions of appropriate stringency. For example, hybridizations may be performed, according to the method of Sambrook et al. 1989, using a hybridization solution comprising: 5×SSC, 5×Denhardt's reagent, 0.5–1.0% SDS, 100 μg/ml denatured, fragmented salmon sperm DNA, 0.05% sodium pyrophosphate and up to 50% formamide. Hybridization is carried out at 37–42' C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42–65° C. in 1×SSC and 1% SDS, changing the solution every 30 minutes.

One common formula for calculating the stringency conditions required to achieve hybridization between nucleic acid molecules of a specified sequence homology is (Sambrook et al., 1989):

$$T_m = 81.5° C. + 16.6 \text{ Log}[Na+] + 0.41(\% G+C) - 0.63(\% \text{ formamide}) - 600/\#bp \text{ in duplex}$$

As an illustration of the above formula, using [Na+]= [0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

Nucleic acids of the present invention may be maintained as DNA in any convenient cloning vector. In a preferred embodiment, clones are maintained in plasmid cloning/expression vector, such as pBluescript (Stratagene, La Jolla, Calif.), which is propagated in a suitable E. coli host cell.

PTX1-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the cDNA comprising the sequence of SEQ ID NO: 1. Such oligonucleotides are useful as probes for detecting or isolating PTX1 genes or homologues in other species.

The nucleic acid sequences referred to above may be modified by addition, substitution, insertion or deletion of one or more nucleotides, but preferably without abolition of ability to hybridize selectively with nucleic acid molecules with the sequence shown in SEQ ID No: 1 or its complementary sequence, that is wherein the degree of homology of the oligonucleotide or polynucleotide with one of the sequences given is sufficiently high.

In some preferred embodiments, oligonucleotides according to the present invention that are fragments of the sequence shown in SEQ ID NO: 1 or its complementary sequence, or allele associated with cancer susceptibility, are at least about 10 nucleotides in length, more preferably at least 15 nucleotides in length, most preferably at least about 20 nucleotides in length. The design of oligonucleotides is well within the capabilities of the skilled person. Preferred oligonucleotides are between 10 and 100 nucleotide bases in length. Such fragments individually represent aspects of the present invention.

Fragments and other oligonucleotides may be used as primers or probes as discussed, but may also be generated (e.g. by PCR) in methods concerned with determining the presence in a test sample of a sequence indicative of cancer susceptibility.

Such oligonucleotide probes or primers, as well as the full-length sequence (and mutants, alleles, variants and derivatives) are also useful in methods screening for a test sample containing nucleic acids for the presence of PTX1, alleles, mutants or variants thereof, especially those that indicate susceptibility or predisposition to cancers, the probes hybridizing with a target sequence from a sample obtained from the individual being tested. The conditions of the hybridization can be controlled to minimize non-specific binding, and preferably stringent to moderately stringent hybridization conditions are employed. The skilled person is readily able to design such probes, label them and devise suitable conditions for the hybridization reactions, assisted by textbooks such as Sambrook et al (1989) and Ausubel et al (1992).

On the basis of amino acid sequence information (SEQ ID NO: 2), oligonucleotide probes or primers may be designed, taking into account the degeneracy of the genetic code. An oligonucleotide for use in nucleic acid amplification may have about 10 or fewer codons (e.g. 6, 7 or 8), i.e. be about 30 or fewer nucleotides in length (e.g. 18, 21 or 24). Generally specific primers are upwards of 14 nucleotides in length, but not more than 18 to 20. Those skilled in the art are well versed in the design of primers for use in processes such as PCR.

Nucleic acid molecules according to the present invention, such as a full-length coding sequence or oligonucleotide probe or primer, may be provided as part of a kit, e.g. in a suitable container such as a vial in which the contents are protected from the external environment. The kit may include instructions for use of the nucleic acid molecules, e.g. in PCR and/or a method for determining the presence of nucleic acids of interest in a test sample. A kit wherein the nucleic acid molecules are intended for use in PCR may include one or more other reagents required for the reaction, such as polymerase, nucleosides, buffer solution etc. The nucleic acid molecules may also be labeled with a detectable label or marker, such as any radioactive, fluorescent, biological or enzymatic tags or labels of standard use in the art. U.S. patents concerning the use of such labels include U.S. Pat. Nos. 3,817,837; 3,850,752; 3,939,350; 3,996,345; 4,277,437; 4,275,149 and 4,366,241, each incorporated herein by reference.

A convenient way of producing a polypeptide according to the present invention is to express nucleic acid molecules encoding it, by use of the nucleic acid molecules in an expression system. This is discussed below. Vectors comprising the nucleic acid molecules of the present invention and host cells containing such vectors and/or nucleic acids according to the invention form further aspects of the present invention.

A host cell containing nucleic acid molecules according to the present invention, e.g. as a result of introduction of the nucleic acid molecule into the cell or into an ancestor of the cell and/or genetic alteration of the sequence endogenous to the cell or ancestor (which introduction may take place in vitro or in vivo), may be comprised (e.g. in the soma) within an organism which is an animal, particularly a mammal, which may be human or non-human, such as a rabbit, cat, dog, pig etc, or which is a bird such as a chicken. Genetically modified or transgenic animals or birds comprising such a cell are also provided as further aspects of the present invention.

The transgenic animals of the present invention may be used as animal disease models to assess therapeutic agents that may be efficacious in the treatment of cancer. However, such modified or transgenic animals are probably more useful in terms of research, particularly genetically modified animals wherein the modification is the deletion ("knockout") or mutation of nucleic acid molecules corresponding to PTX1 or an allele thereof.

B. Proteins

A full-length PTX1 protein of the present invention may be prepared in a variety of ways, according to known methods. The protein may be purified from appropriate sources, e.g., human or animal cultured cells or tissues, by immunoaffinity purification.

The availability of nucleic acid molecules encoding PTX1 or splice variants thereof enables production of the encoded proteins using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md.

Alternatively, according to a preferred embodiment, larger quantities of PTX1 may be produced by expression in a suitable prokaryotic or eukaryotic system. For example, part or all of a DNA molecule, such as the cDNA having SEQ ID NO: 1, may be inserted into a plasmid vector adapted for expression in a bacterial cell, such as *Escherichia coli*, and yeast cells, such as *Saccharomyces cerevisiae*, or into a baculovirus vector for expression in insect cells. Such vectors comprise the regulatory elements necessary for expression of the DNA in the host cell (e.g. *E. coli* or insect cell), positioned in such a manner as to permit expression of the DNA in the host cell. Such regulatory elements required for expression include promoter sequences, transcription initiation and termination sequences, and, optionally, enhancer sequences.

The PTX1 protein produced by nucleic acid expression in a recombinant prokaryotic or eukaryotic system may be purified according to methods known in the art. In a preferred embodiment, a commercially available expression/secretion system may be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6–8 histidine residues at their N-terminus or C-terminus. In yet another embodiment, GST fusion proteins may be employed to facilitate purification. Such methods are commonly used by those experienced in the field of recombinant protein purification.

The PTX1 proteins of the invention, prepared by the aforementioned methods, may be analyzed according to standard procedures. For example, such proteins may be subjected to amino acid sequence analysis, and/or gel electrophoresis.

As discussed above, the present invention also provides PTX1 polypeptides, or fragments or active portions thereof, for use in pharmaceuticals, in the development of drugs, diagnostic kits and for further study into its properties and role in vivo.

Polypeptides which are amino acid sequence variants, alleles, derivatives or mutants are also provided by the present invention. A polypeptide that is a variant, allele, derivative or mutant may have an amino acid sequence which differs from that given in SEQ ID NO: 2 by addition, substitution, deletion and insertion of one or more amino acids. Preferred such polypeptides have PTX1 function, that is to say have one or more of the following properties: immunological cross-reactivity with an antibody reactive with the polypeptides for which the sequence is set out in SEQ ID NO: 2 and sharing an epitope with the polypeptides for which the amino acid sequence is set out in SEQ ID NO: 2 (as determined, for example, by immunological cross-reactivity between the two polypeptides).

A polypeptide which is an amino acid sequence variant, allele, derivative or mutant of the amino acid sequence shown in SEQ ID NO: 2 may comprise an amino acid sequence which shares greater than about 35% sequence identity with the sequence shown, greater than about 40%, greater than about 50%, greater than about 60%, greater than about 70%, greater than about 80%, greater than about 90% or greater than about 95%. Particular amino acid sequence variants may differ from that shown in SEQ ID NO. 2 by insertion, addition, substitution or deletion of 1 amino acid, 2, 3, 4, 5–10, 10–20, 20–30, 30–40, 40-50, 50–100, 100–150, or more than 150 amino acids. For amino acid "homology/identity", this may be understood to be similarity (according to the established principles of amino acid similarity, e.g., as determined using the algorithm GAP (Genetics Computer Group, Madison, Wis.) or identity. GAP uses the Needleman and Wunsch algorithm to align two complete sequences that maximizes the number of matches and minimizes the number of gaps. Generally, the default parameters are used, with a gap creation penalty=12 and gap extension penalty=4. Use of GAP may be preferred but other algorithms may be used including without limitation, BLAST (Altschul et al. (1990 J. Mol. Biol. 215:405–410); FASTA (Pearson and Lipman (1998) PNAS USA 85:2444–2448) or the Smith Waterman algorithm (Smith and Waterman (1981) J. Mol. Biol. 147:195–197) generally employing default parameters. Use of either of the terms "homology" and "homologous" herein does not imply any necessary evolutionary relationship between the compared sequences. The terms are used as they are in the phrase "homologous recombination", i.e., the terms merely require that the two nucleotide sequences are sufficiently similar to recombine under appropriate conditions.

A polypeptide according to the present invention may be used in screening for molecules which modulate its activity or function. Such molecules may be useful in a therapeutic (possibly including prophylactic) context.

The present invention also provides antibodies capable of immunospecifically binding to proteins of the invention. Polyclonal antibodies directed toward PTX1 may be prepared according to standard methods. In a preferred embodiment, monoclonal antibodies are prepared, which react immunospecifically with various epitopes of PTX1. Monoclonal antibodies may be prepared according to general methods of Köhler and Milstein, following standard protocols. Polyclonal or monoclonal antibodies that immunospecifically interact with PTX1 can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules. Other uses of anti-PTX1 antibodies are described below.

Antibodies according to the present invention may be modified in a number of ways. Indeed the term "antibody" should be construed as covering any binding substance having a binding domain with the required specificity. Thus, the invention covers antibody fragments, derivatives, functional equivalents and homologues of antibodies, including synthetic molecules and molecules whose shape mimics that of an antibody enabling it to bind an antigen or epitope.

Exemplary antibody fragments, capable of binding an antigen or other binding partner, are Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulfide bridge at the hinge region. Single chain Fv fragments are also included.

Humanized antibodies in which CDRs from a non-human source are grafted onto human framework regions, typically with alteration of some of the framework amino acid residues, to provide antibodies which are less immunogenic than the parent non-human antibodies, are also included within the present invention.

III. Uses of PTX1-Encoding Nucleic Acids, PTX1 Proteins and Antibodies Thereto

The identification of the tumor suppressor gene, PTX1, provides utility for diagnosis, prognosis and gene therapy of prostate cancer. Isolation of PTX1-encoding nucleic acids, proteins and antibodies thereto will also provide wide utility as prognostic indicators of neoplastic disease and as therapeutic agents for the treatment of many types of cancer.

Additionally, PTX1-related nucleic acids, proteins, and antibodies thereto, in accordance with this invention, may be used as research tools to identify other tumor suppressor genes.

A. PTX1-Encoding Nucleic Acids

PTX1-encoding nucleic acids may be used for a variety of purposes in accordance with the present invention. PTX1-encoding DNA, RNA, or fragments thereof may be used as probes to detect the presence of and/or expression of genes encoding the PTX1 protein. Methods in which PTX1-encoding nucleic acids may be utilized as probes for such assays include, but are not limited to: (1) in situ-hybridization; (2) Southern hybridization (3) Northern hybridization; and (4) assorted amplification reactions such as polymerase chain reactions (PCR).

The PTX1-encoding nucleic acids of the invention may also be utilized as probes to identify related genes from other species as demonstrated herein. As is well known in the art, hybridization stringencies may be adjusted to allow hybridization of nucleic acid probes with complementary sequences of varying degrees of homology. Thus, PTX1-encoding nucleic acids may be used to advantage to identify and characterize other genes of varying degrees of relation to PTX1, thereby enabling further characterization of the observed altered gene expression involved in the aggressive progression of prostate cancer. Additionally, they may be used to identify genes encoding proteins that interact with PTX1 (e.g., by the "interaction trap" technique; see U.S. Pat. No. 5,580,736), which should further accelerate elucidation of these cellular signaling mechanisms which are involved in cancer progression (Golemis et al. 1996).

Nucleic acid molecules, or fragments thereof, encoding PTX1 may also be utilized to control the production of PTX1, thereby regulating the amount of protein available to participate in disease signaling pathways. Alterations in the physiological amount of PTX1 protein may act synergistically with other agents used to halt tumor progression. In disease models of prostate cancer, the nucleic acid molecules of the invention may be used to decrease expression of PTX1. In this embodiment, antisense molecules are employed which are targeted to expression-controlling sequences of PTX1-encoding genes. Antisense oligonucleotides may be designed to hybridize to the complementary sequence of nucleic acid, pre-mRNA or mature mRNA, interfering with the production of polypeptide encoded by a given DNA sequence (e.g. either native PTX1 polypeptide or a mutant or variant form thereof), so that its expression is reduced or prevented altogether. In addition to the PTX1 coding sequence, antisense techniques can be used to target the control sequences of the PTX1 gene, e.g. the 5' flanking sequence of the PTX1 coding sequence such as the translation start site. Antisense oligomers should be of sufficient length to hybridize to the target nucleotide sequence and exert the desired effect, e.g. blocking translation of a mRNA molecule. However, it should be noted that smaller oligomers are likely to be more efficiently taken up by cells in vivo such that a greater number of antisense oligomers may be delivered to the location of the target mRNA. Preferably, antisense oligomers should be at least 15 nucleotides long to achieve adequate specificity. Oligonucleotides for use in antisense technology are preferably between 15 to 30 nucleotides in length. The use of antisense molecules to decrease expression levels of a pre-determined gene is known in the art. The construction of antisense sequences and their use is described in Peyman and Ulman, Chemical Reviews, 90:543–584, (1990), Crooke, Ann. Rev. Pharmacol. Toxical., 32:329–376, (1992), and Zamecnik and Stephenson, P.N.A.S., 75:280–284, (1974). Antisense constructs may be generated which contain the entire PTX1 cDNA in reverse orientation.

In another embodiment, overexpression of the PTX1 gene will be introduced into prostate cancer cells in experiments to assess restoration of PTX1 activity in such cells as overexpression can lead to overproduction of the encoded protein, PTX1. Overproduction of PTX1 in cells may be assessed by immunofluorescence or any other standard technique known in the art. Alternatively, overexpression of PTX1 by this method may facilitate the isolation and characterization of other components involved in the protein-protein complex formation that occurs as a cell progressively becomes more malignant.

As described above, PTX1-encoding nucleic acids are also used to advantage to produce large quantities of substantially pure PTX1 protein, or selected portions thereof.

B. PTX1 Protein and Antibodies

Purified PTX1 protein, or fragments thereof, may be used to produce polyclonal or monoclonal antibodies which also may serve as sensitive detection reagents for the presence and accumulation of PTX1 (or complexes containing PTX1) in biopsy samples or cultured cells. Recombinant techniques enable expression of fusion proteins containing part or all of the PTX1 protein. The full length protein or fragments of the protein may be used to advantage to generate an array of monoclonal antibodies specific for various epitopes of the protein, thereby providing even greater sensitivity for detection of the protein in prostate cells.

Polyclonal or monoclonal antibodies immunologically specific for PTX1 may be used in a variety of assays designed to detect and quantitate the protein. Such assays include, but are not limited to: (1) flow cytometric analysis; (2) immunochemical localization of PTX1 in prostate cells; and (3) immunoblot analysis (e.g., dot blot, Western blot) of extracts from prostate cells. Additionally, as described above, anti-PTX1 can be used for purification of PTX1 (e.g., affinity column purification, immunoprecipitation).

From the foregoing discussion, it can be seen that PTX1-encoding nucleic acids, PTX1 expressing vectors, PTX1 proteins and anti-PTX1 antibodies of the invention can be used to detect PTX1 gene expression and alter PTX1 protein accumulation for purposes of assessing those patients at risk for prostate progression. The invention also provides materials that facilitate the elucidation of the genetic and protein interactions involved in the regulation of the disease progression as a normal prostate cell gives rise to a malignant tumor.

Exemplary approaches for detecting PTX1-encoding nucleic acid molecules or polypeptides/proteins include:

a) determining the presence, in a sample from a patient, of nucleic acid molecules according to the present invention; or b) determining the presence, in a sample from a patient, of the polypeptide encoded by the PTX1 gene and, if present, determining whether the polypeptide is full length, and/or is mutated, and/or is expressed at the normal level; or c) using DNA restriction mapping to compare the restriction pattern produced when a restriction enzyme cuts a sample of nucleic acid molecules from the patient with the restriction pattern obtained from the PTX1-encoding nucleic acid sequence; or, d) using a specific binding member capable of binding to a PTX1 nucleic acid sequence, the specific binding member comprising nucleic acid hybridizable with the PTX1 sequence, or substances comprising an antibody domain with specificity for a PTX1 nucleic acid sequence or the polypeptide encoded by it, the specific binding member being labeled so that binding of the specific binding member to its binding partner is detectable; or e) using PCR involving one or more primers based on PTX1 nucleic acid sequences to screen for PTX1 sequences in a sample from a patient.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples and they do not need to be listed here. Further, the term "specific binding pair" is also applicable where either or both of the specific binding member and the binding partner comprise a part of a large molecule. In embodiments in which the specific binding pair are nucleic acid sequences, they will be of a length to hybridize to each other under conditions of the assay, preferably greater than 10 nucleotides long, more preferably greater than 15 or 20 nucleotides long.

In most embodiments for screening for cancer susceptibility alleles, the PTX1-encoding nucleic acid molecules in the sample will initially be amplified, e.g. using PCR, to increase the amount of the analyte as compared to other sequences present in the sample. This allows the target sequences to be detected with a high degree of sensitivity if they are present in the sample. This initial step may be avoided by using highly sensitive array techniques that are becoming increasingly important in the art.

The identification of the PTX1-encoding nucleic acid sequence and its association with prostate cancer paves the way for aspects of the present invention to provide the use of materials and methods, such as are disclosed and discussed above, for establishing the presence or absence in a test sample of a variant form of the PTX1-encoding nucleic acid molecule, in particular an allele or variant specifically associated with cancer, especially prostate cancer. This may be for diagnosing a predisposition of an individual to cancer. It may be for diagnosing cancer of a patient with the disease as being associated with PTX1.

This allows for planning of appropriate therapeutic and/or prophylactic measures, permitting stream-lining of treatment. The approach further stream-lines treatment by targeting those patients most likely to benefit.

According to another aspect of the invention, methods of screening drugs for cancer therapy to identify suitable drugs for restoring PTX1 product function are provided. Restoration of PTX1 function by gene transfer or by pharmacological means (e.g., small molecules which mimic PTX1 structure and/or function) would be expected to ameliorate the aberrant growth characteristics of prostate cancer cells.

The PTX1 polypeptide or fragment employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between a PTX1 polypeptide or fragment and the agent being tested, or examine the degree to which the formation of a complex between a PTX1 polypeptide or fragment and a known ligand is interfered with by the agent being tested.

Another technique for drug screening provides high throughput screening for compounds having suitable binding affinity to the PTX1 polypeptides and is described in detail in Geysen, PCT published application WO 84/03564, published on Sep. 13, 1984. Briefly stated, large numbers of different, small peptide test compounds are synthesized on a solid substrate, such as plastic pins or some other surface. The peptide test compounds are reacted with PTX1 polypeptide and washed. Bound PTX1 polypeptide is then detected by methods well known in the art.

Purified PTX1 can be coated directly onto plates for use in the aforementioned drug screening techniques. However, non-neutralizing antibodies to the polypeptide can be used to capture antibodies to immobilize the PTX1 polypeptide on the solid phase.

This invention also contemplates the use of competitive drug screening assays in which neutralizing antibodies capable of specifically binding the PTX1 polypeptide compete with a test compound for binding to the PTX1 polypeptide or fragments thereof. In this manner, the antibodies can be used to detect the presence of any peptide which shares one or more antigenic determinants of the PTX1 polypeptide.

A further technique for drug screening involves the use of host eukaryotic cell lines or cells (such as described above) which have a nonfunctional PTX1 gene. These host cell lines or cells are defective at the PTX1 polypeptide level. The host cell lines or cells are grown in the presence of drug compound. The rate of growth of the host cells is measured to determine if the compound is capable of regulating the growth of PTX1 defective cells.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9: 19–21. In one approach, one first determines the three-dimensional structure of a protein of interest (e.g., PTX1 polypeptide) or, for example, of the PTX1-DNA complex, by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527–533). In addition, peptides (e.g., PTX1 polypeptide) may be analyzed by an alanine scan (Wells, 1991) Meth. Enzym. 202:390–411. In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacore.

Thus, one may design drugs which have, e.g., improved PTX1 polypeptide activity or stability or which act as inhibitors, agonists, antagonists, etc. of PTX1 polypeptide activity. By virtue of the availability of cloned PTX1 sequences, sufficient amounts of the PTX1 polypeptide may be made available to perform such analytical studies as x-ray crystallography. In addition, the knowledge of the PTX1 protein sequence provided herein will guide those employing computer modeling techniques in place of, or in addition to x-ray crystallography.

The present invention further provides "compositions" in biological compatible solution, pharmaceutically acceptable excipient, carrier, buffer, stabilizer or other materials well known to those skilled in the art, comprising the nucleic acids, polypeptides, vectors or antibodies of the invention. A biologically compatible solution is a solution in which the polypeptide, nucleic acid, vector, or antibody of the invention is maintained in an active form, e.g. in a form able to effect a biological activity. Generally, such a biologically compatible solution will be an aqueous buffer, e.g. Tris, phosphate, or HEPES buffer, containing salt ions. Usually the concentration of salt ions will be similar to physiological levels. Biologically compatible solutions may include stabilizing agents and preservatives.

Such compositions may be formulated for administration by topical, oral, parenteral, intranasal, subcutaneous, and intraocular routes. Parenteral administration is meant to include intravenous injection, intramuscular injection, intraarterial injection or infusion techniques. The compositions may be administered parenterally in dosage unit formulations containing standard well known non-toxic physiologically acceptable carriers, adjuvants and vehicles as desired.

The preferred sterile injectable preparations may be a solution or suspension in a nontoxic parenterally acceptable solvent or diluent. Examples of pharmaceutically acceptable carriers are saline, buffered saline, isotonic saline (e.g. monosodium or disodium phosphate, sodium, potassium, calcium or magnesium chloride, or a mixture or such salts), Ringers solution, dextrose, water, sterile water, glycol, ethanol, and combinations thereof. 1,3-butanediol and sterile fixed oils are conveniently employed as solvents or suspending media. Any bland fixed oil may be employed including synthetic mono- or di-glycerides. Fatty acids such as oleic acid also find use in the preparation of injectables.

The composition medium may also be a hydrogel which is prepared from any biocompatible or non-cytotoxic (homo or hetero) polymer, such as a hydrophilic polyacrylic acid polymer that can act as a drug adsorbing sponge. Such polymers have been described, for example in application WO93/08845, the entire contents of which are hereby incorporated by reference. Certain of them, such as, in particular, those obtained from ethylene and/or propylene oxide are commercially available. A hydrogel may be deposited directly onto the surface of the tissue treated, for example during surgical intervention.

The present invention provides "methods of treatment" which comprise the administration to a human or other animal of an effective amount of a composition of the invention.

Effective amounts vary, depending on the age, type and severity of the condition to be treated, body weight, desired duration of treatment, method of administration, and other parameters. Effective amounts are determined by a physician or other qualified medical professional.

The PTX1 polypeptides of the invention may also be administered via intra-tumor injection in a biologically compatible buffer, in doses of about 0.01 mg/kg to about 100 mg/kg, preferably about 0.1 mg/kg to about 50 mg/kg, and most preferably about 1 mg/kg to about 10 mg/kg of body weight per day. Alternatively, nucleic acids expressing the peptides of the invention may be delivered directly to a tumor in vectors or liposomes which facilitate entry into a prostate tumor cancer cell.

The following examples provide illustrative methods of practicing the instant invention, and are not intended to limit the scope of the invention in any way.

EXAMPLE 1

Identification of PTX1, A Candidate Tumor Suppressor Gene on Chromosome 12

This example describes the use of subtractive hybridization to identify a novel gene, PTX1, which maps to Chromosome 12 and is present in normal prostate but not in prostate carcinoma.

I. Materials and Methods

The following protocols are provided to facilitate the practice of the present invention.

Subtractive Hybridization

Total RNA was extracted from human normal prostate (kindly provided by the National Diabetes Research Interchange) and prostate carcinoma (remnant pathological specimen from our department) according to Chomczynski and Sacchi (1987). Poly A$^+$ mRNA was purified from total RNA using an Oligotex mRNA Mini Kit (Qiagen). Subtractive hybridization was carried out using the PCR-Select cDNA Subtraction Kit (Clontech Laboratories), and the procedure provided by the manufacturer was followed exactly. The normal prostate cDNA was used as 'tester' and the prostate tumor cDNA as 'driver'. After hybridization to remove common sequences, the differentially expressed cDNAs that are present in the tester cDNA, but absent from the driver cDNA, were amplified with Pfu DNA polymerase. The PCR products were phosphorylated with T4 polynucleotide kinase, blunt-end ligated to SmaI-cleaved, dephosphorylated pUC18 vector (Amersham Pharmacia Biotech), and transformed into XL1-Blue competent cells (Stratagene). Mini-preparations of plasmid DNA from randomly picked colonies were screened in a dot-blot format with subtracted probes as described in the manual accompanying the PCR-Select Differential Screening Kit (Clontech Laboratories). Positive clones were further screened by nucleotide sequence analysis.

5'- and 3'-Race

To isolate a full-length cDNA, the SMART RACE cDNA Amplification Kit (Clontech Laboratories) was used. Poly A$^+$ mRNA was isolated from 230 μg normal prostate total RNA using the Oligotex mRNA Mini Kit (Qiagen). Half of the poly A$^+$ RNA was used for the synthesis of 5'-RACE ready cDNA and the other half for 3'-RACE ready cDNA. The 5'- and 3'-RACE were carried out according to the manual of the SMART RACE cDNA Amplification Kit. The PCR fragments were subcloned into pUC18 as described above.

Tissue Expression of PTX1

Expression of PTX1 in human tissues was examined by RT-PCR using first strand cDNAs (Human Multiple Tissue cDNA Panels I and II) purchased from Clontech Laboratories, Inc. Aliquots of 5 μl of the cDNA were amplified using PTX1-specific or β-actin-specific primers in a total volume of 75 μl. PCR conditions were: 1 cycle of 96° C. for 1 min; 35 cycles of 94° C. for 1 min, 59° C. for 1 min, and 72° C. for 2 min; followed by 1 cycle of 72° C. for 7 min. Aliquots of 20 μl of the PCR products were analyzed on 2% agarose gel. The tissues tested were: brain, heart, kidney, liver, lung, pancreas, placenta, skeletal muscle, colon, ovary, peripheral blood leukocytes, prostate, small intestine, spleen, testis and thymus.

Human Chromosome Localization of the PTX1 Gene

Monochromosomal Somatic Cell Hybrid PCRable DNAs (Quantum Biotechnologies) were used to localize PTX1 gene on human chromosomes. Aliquots of 250 ng DNA of a panel of 24 hybrids and 3 controls were amplified with PTX1-specific primers in a total volume of 75 μl. PCR conditions were: 1 cycle of 96° C. for 1 min; 30 cycles of 94° C. for 1 min, 55° C. for 1 min, and 72° C. for 2 min; followed by 1 cycle of 72° C. for 7 min. Aliquots of 10 μl of the PCR products were analyzed on 1% agarose gel.

Expression of Recombinant PTX1 and Production of Antiserum

The coding sequence corresponding to residues 121–208 of the PTX1 protein was amplified using synthetic primers with a built-in Nco I site at the 5'-end and a Bam HI site at the 3'-end. The amplified fragment was purified from agarose gel and subcloned into the Nco I/Bam HI sites of the bacterial expression plasmid vector, pCAL-c (Stratagene). To facilitate the purification of the recombinant protein, the sequence of pCAL-c vector between the Bam HI and Kpn I sites was replaced with one containing six consecutive His codons followed by a stop codon. The expression plasmid was transformed into BL21-CodonPlus (DE3)-RIL competent cells (Stratagene).

To produce the recombinant PTX1 protein, bacteria harboring the expression plasmid were grown in 200 ml of LB medium containing 100 μg/ml of ampicillin to an OD$_{600}$ of 0.6–1.0, and induced for 2 hr with 2 mM IPTG. The cells were harvested, lysed with 20 ml of B-Per Reagent (Pierce) and the inclusion bodies were collected by centrifugation and washed three times with 1/10 dilution of B-Per Reagent. The recombinant protein was extracted from the inclusion bodies with 10 ml of extraction buffer (6M guanidine HCl, 50 mM sodium phosphate, 300 mM NaCl, 5 mM mercaptoethanol, pH 8.0) overnight at 4° C. The protein extract was mixed with 1 ml of pre-equilibrated Talon Metal Affinity Resin (Clontech Laboratories, Inc) at room temperature for 20 min. The resin was washed twice with 10 ml of wash buffer (6M guanidine HCl, 50 mM sodium phosphate, 300 mM NaCl, 5 mM imidazole, 5 mM mercaptoethanol, pH 7.0) and packed into a small column. The column was washed 3 times with 5 ml of wash buffer, and then eluted with 5 ml of elution buffer (6M guanidine HCl, 50 mM sodium phosphate, 300 mM NaCl, 150 mM imidazole, pH 7.0). The purified protein was dialyzed at 4° C. against 3×4 liters of 10 mM ammonium bicarbonate and lyophilized. The dried protein was sent to Alpha Diagnostic International for custom production of polyclonal antibodies in rabbits.

Immunohistochemical Localization of PTX1

The procedure was carried out at room temperature except where indicated. Human prostate carcinoma sections were deparaffinized 3 times in xylene for 5 min each, rehydrated in graded ethanol, and boiled in antigen retrieval solution (10 mM sodium citrate/citric acid, pH 6.0) at a pressure of 15 psi for 10 min. The sections were washed twice with Buffer 1 (100 mM Tris HCl, 150 mM NaCl, pH 7.5) for 5 min each. They were incubated with 200 μl of blocking solution (1% Blocking Reagent [Roche Biochemical], 100 mM maleic acid, 150 mM NaCl, pH 7.5) for 1 hr, followed by 200 μl of 2% goat serum in blocking solution for 30 min. They were then incubated with 100 μl of primary antiserum (1:100 dilution in blocking solution) for 1 hr. After washing 3 times with Buffer 1 for 5 min the sections were incubated with 100 μl of goat anti-rabbit IgG/alkaline phosphatase conjugate (1:100 dilution in blocking solution) for 1 hr. The sections were washed 3 times with Buffer 1 for 5 min, once with AP Buffer (100 mM Tris HCl, 150 mM NaCl, 50 mM $MgCl_2$, pH 9.5), and then incubated with 200 μl of freshly prepared Vega Red Chromogen (Biomeda Corp) for 30–60 min. Finally, the sections were counterstained with hematoxylin, dehydrated in graded ethanol, clarified in xylene and mounted in Permount (Fisher Scientific).

II. Results

Molecular Cloning and Characterization of PTX1 cDNA

A large number of clones were obtained from the subtractive hybridization. Of the 396 randomly picked colonies, 57 were found positive by dot blot hybridization with a subtracted cDNA probe. They were further screened by nucleotide sequence analysis. Of these 57 clones, 56% were semenogelin cDNA. The other clones were mitochondrial DNA (11%), 28S ribosomal RNA (7%), prolactin-inducible protein (7%) and mucin (5%). The remaining clones (14%) were unique sequences. Four of these clones (#149, 341, 348 and 394) were novel sequences. RT-PCR using normal prostate and prostate tumor cDNAs showed that clones 149 and 348 were cDNAs differentially expressed in normal prostate (FIG. 1). Clone 348 was selected for further characterization and was re-named PTX1.

Since clone 348 is only 167 bp long, the full-length cDNA was isolated using 5'- and 3'-RACE. The 5'-RACE yielded a 180 bp fragment, while the 3'-RACE produced a 1.3 kb fragment. The composite nucleotide sequence of these two clones comprises a cDNA sequence of 1327 bp (SEQ ID NO: 1), including 26 bp of poly(A) tail at the 3' end (FIG. 2). A continuous open reading frame is present, starting from the ATG codon at base 87 and ending at the TAA codon at base 1218. There are three other possible ATG codons upstream at bases 21, 51, and 59, but use of these codons gives rise to terminated proteins. Hence, the nucleotide sequence appears to encode a protein of 377 amino acid residues (SEQ ID NO: 2). The 5'-untranslated region-is 86 base pairs (bp) long. On the other hand, the 3'-untranslated region is 107 bp long and contains one AATAAA sequence between bases 1278 and 1283. This sequence is only 18 bp upstream of the poly(A) tail and is apparently used for RNA processing and polyadenylation (Proudfoot and Brownlee, 1976).

Tissue Expression and Chromosomal Localization of PTX1 Gene

Figure 3:
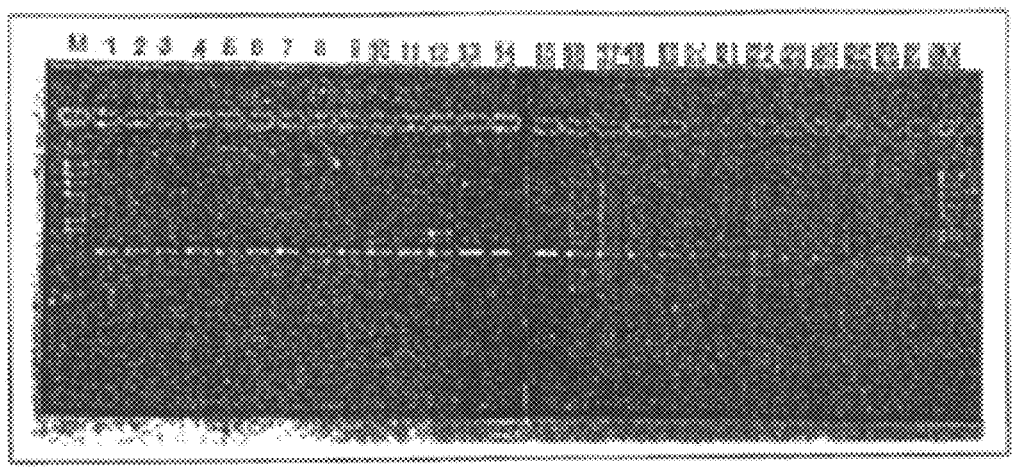
FIG. 3 is a gel showing that the PTX1 gene is localized to human chromosome 12. DNA samples of a panel of 24 somatic cell hybrids and 3 genomic DNA controls were amplified with PTX1-specific primers as described in the Methods. The PCR products were analyzed on a 1% agarose gel. DNA samples in lanes 1, 2, 3, 5, 6, 7, 8, 9, 10, 11, 12, 13, 14, 15, 16, 17, 18, 19, 21, 22 contain a single human chromosome corresponding to the number. The sample in lane 4 contains two human chromosomes, 4 and 7. The sample in lane 20 contains three chromosomes, 20, 8, and 4. Samples in lanes 23, 24, 25, 26, and 27 contain chromosome X, chromosome Y, human DNA, hamster DNA, and mouse DNA, respectively. Molecular size markers (M) were Lambda DNA digested with Hind III. Only the samples containing human chromosome 12 and human DNA produced a 2 kb band (lanes 12 and 25), which demonstrates that the PTX1 gene is localized on human chromosome 12. The smaller size band that is present in all lanes (except lane 25) may be related to the rodent PTX1 gene.

Expression study by RT-PCR using PTX1-specific primers and human multiple tissue cDNA panels showed that PTX1 was expressed in all of the 16 human tissues tested (data not shown). The chromosomal localization study by PCR using a monochromosomal somatic cell hybrid panel produced a band of the expected size only in samples containing human chromosome 12 or human genomic DNA control (FIG. 3). These results indicate that the PTX1 gene is localized on human chromosome 12.

Bacterial Expression and Immunolocalization of PTX1 Protein

Figure 4:
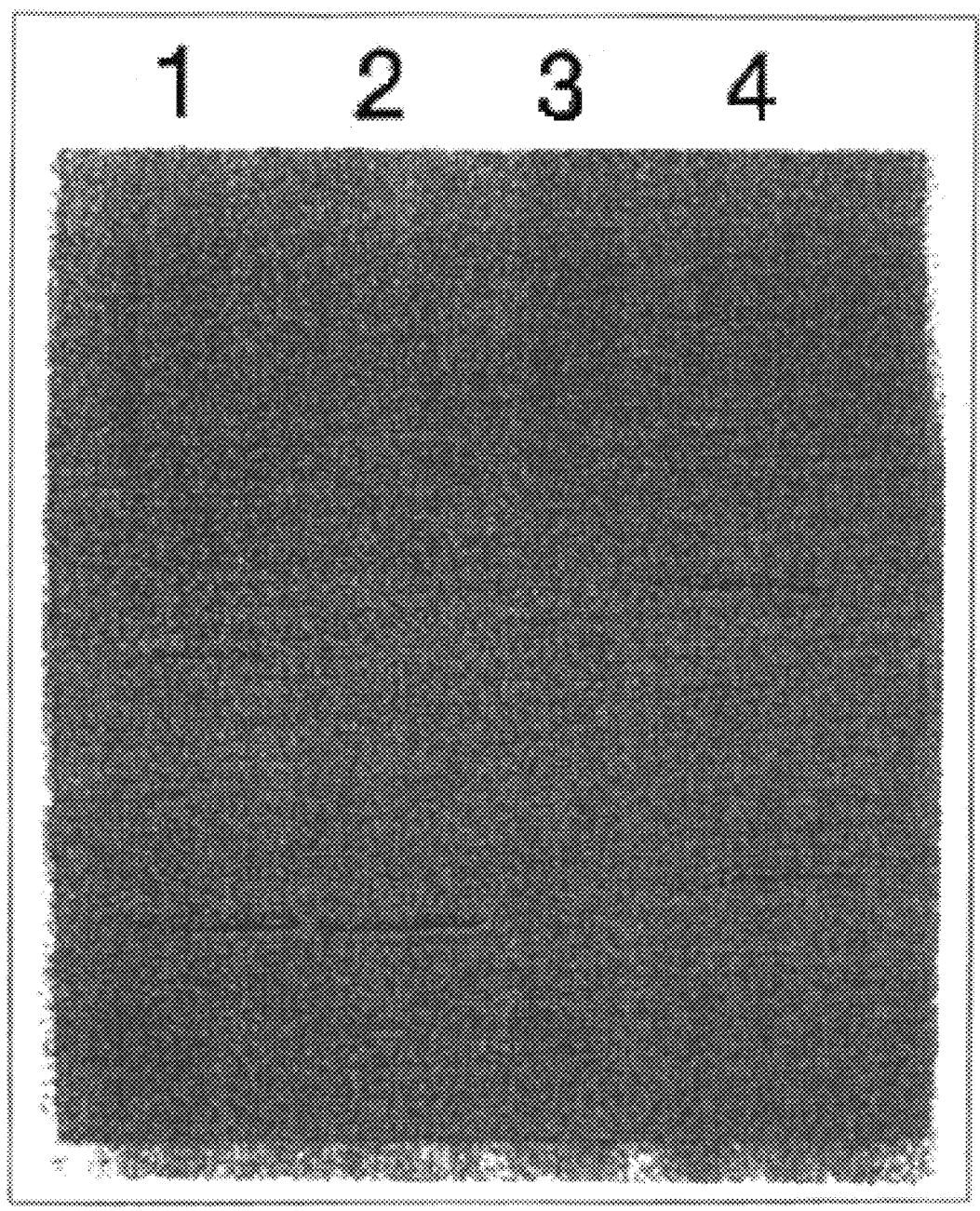
FIG. 4 is a gel showing the purification of the recombinant PTX1 protein on Talon Metal Affinity Resin column. The recombinant protein was extracted from the bacterial host and purified on the Talon Metal Affinity Resin column as described in Example 1. Lane 1 contained total protein; lane 2 contained the first elution of recombinant PTX1 protein; lane 3 contained the second elution of PTX1 protein; and lane 4 contained molecular weight markers.

To generate specific antibodies against PTX1, a segment of the PTX1 sequence was initially expressed in a pCAL-c expression vector as a 12.4 kDa fusion protein with a calmodulin-binding peptide (CBP) tag. However, the fusion protein became insoluble after it was allowed to refold as described by Reddy et al. (1992) and was dialyzed to remove the guanidine HCl. This made it impossible to purify the fusion protein with the calmodulin resin. To obviate this problem, the thombin cleavage sequence of the pCAL-c vector was replaced with one containing six consecutive His codons, followed by a stop codon. This facilitates the purification of the recombinant protein with Talon metal affinity resin under denaturing conditions (FIG. 4). Approximately 3 mg of recombinant protein may be routinely obtained from 200 ml culture using this method.

Figure 5:
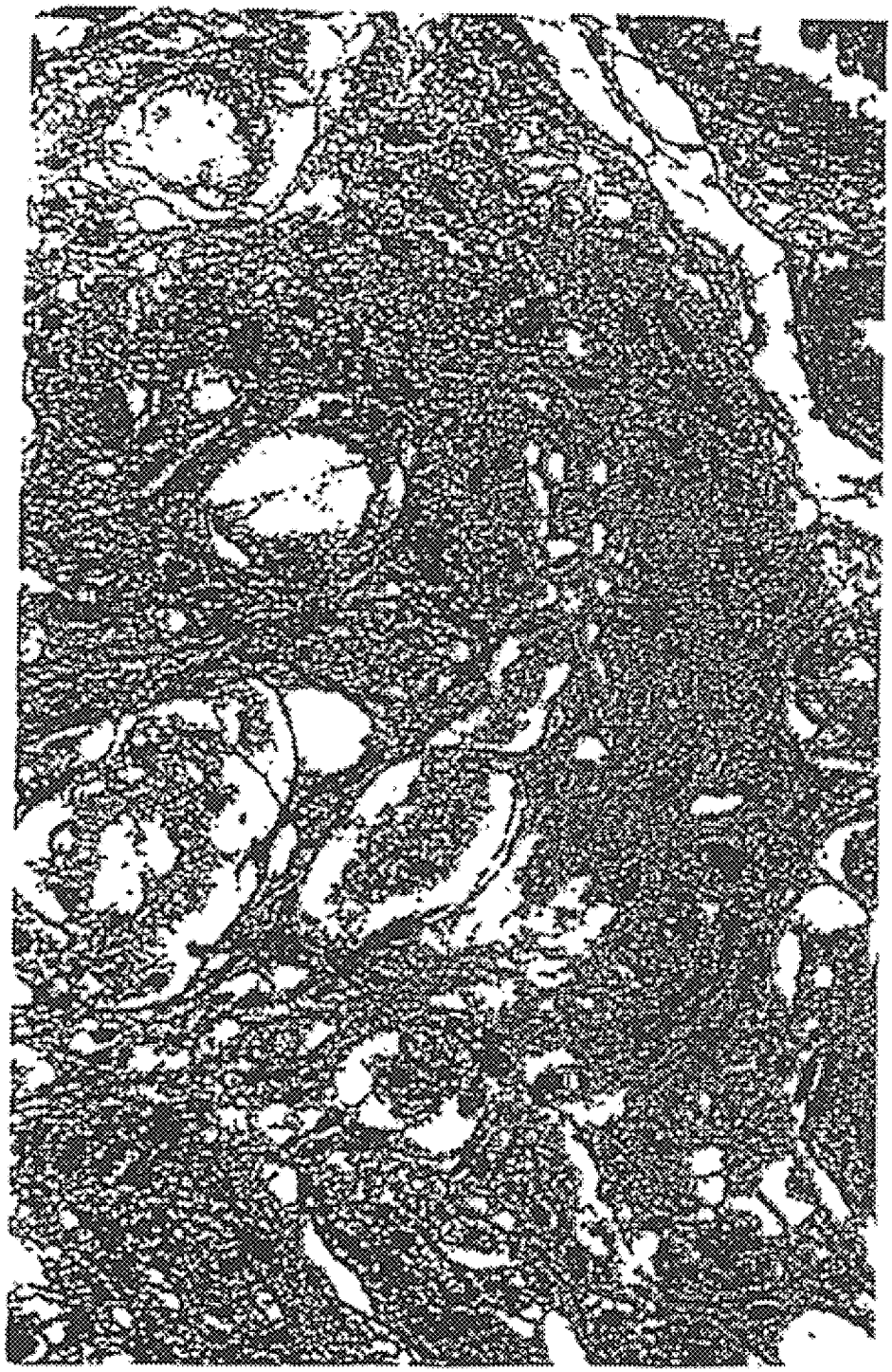
FIG. 5 is a micrograph showing the immunolocalization of PTX1 protein in normal prostate and prostate tumor. The sections were stained for the presence of PTX1 using a rabbit antiserum against recombinant human PTX1. The red color indicates a positive immunoreactive product. Both the cytoplasm and nuclei of the normal glandular epithelium showed strong staining, while the tumor area showed no staining.

Immunohistochemical analysis of sections of human prostate and prostate tumor tissue using an antiserum against PTX1 showed that the cytoplasm and nuclei of the glandular epithelia of the normal prostate were stained, while those of prostate tumor were negative (FIG. 5). Immunostaining using preimmune serum on sections of normal prostate also gave a negative result (data not shown). This indicates that the immunostaining of normal prostate by PTX1 antiserum was specific.

PC-3 Prostate Tumor Cell Line Expression of PTX1 Gene

To elucidate the function of PTX1, the coding sequence of the PTX1-encoding nucleic acid molecule was inserted in both "sense" and "antisense" orientations in a tetracycline-repressible expression plasmid, pTRE2 (Tet-Off Gene Expression System; Clontech Laboratories). The resulting expression constructs were co-transfected with pTK-Hyg plasmid into a G418-resistant, Tet-Off-transfected PC-3 prostate tumor cell line. Stable transfectants were then selected with G418 and hygromycin. Induction of the antisense or sense PTX1 RNA was accomplished by removing tetracycline from the culture medium. Upon induction, both the proliferation rate and the number of viable cells of the cells transfected with the sense PTX1 construct decreased, where as the cells transfected with the antisense PTX1 construct grew faster than the control cells (PC-3 cells transfected with a luciferase expression construct). The growth curves of the PC-3 cells transfected with sense, antisense and luciferase constructs are provided in FIG. 8. The induction of sense and antisense PTX1 RNA was confirmed by RT-PCR using primers specific for PTX1 and the expression vector. The effect of induced RNA on PTX1 translation was also confirmed by immuno-histochemistry (data not shown).

In soft agar assays, cells transfected with the antisense PTX1 construct readily formed colonies, while cells transfected with luciferase or sense PTX1 constructs formed little or no colonies. These results indicate that PTX1 may be a suppressor protein for anchorage-independent cell proliferation.

III. Discussion

The present invention is directed to the isolation and sequence characterization of a full-length cDNA, PTX1, encoding a novel human nuclear protein. This cDNA was selected on the basis that it was expressed in normal prostate, but not in prostate carcinoma. It is ubiquitously expressed in normal human tissues. Its expression in prostate carcinoma is down-regulated, which has been confirmed by both RT-PCR and immunohistochemical analysis. The deduced protein sequence contains a RRLNRKK sequence (SEQ ID NO: 3) which is a putative bipartite nuclear localization signal (Melchior and Gerace, 1995). The nuclear localization of PTX1 has been confirmed by immunohistochemical analysis. Furthermore, it is highly conserved as the human PTX1-specific primers can also detect the rodent counterparts (FIG. 3). Nuclear localization and down-regulation of PTX1 in prostate carcinoma suggests that PTX1 is a candidate tumor suppressor gene.

Figure 6:
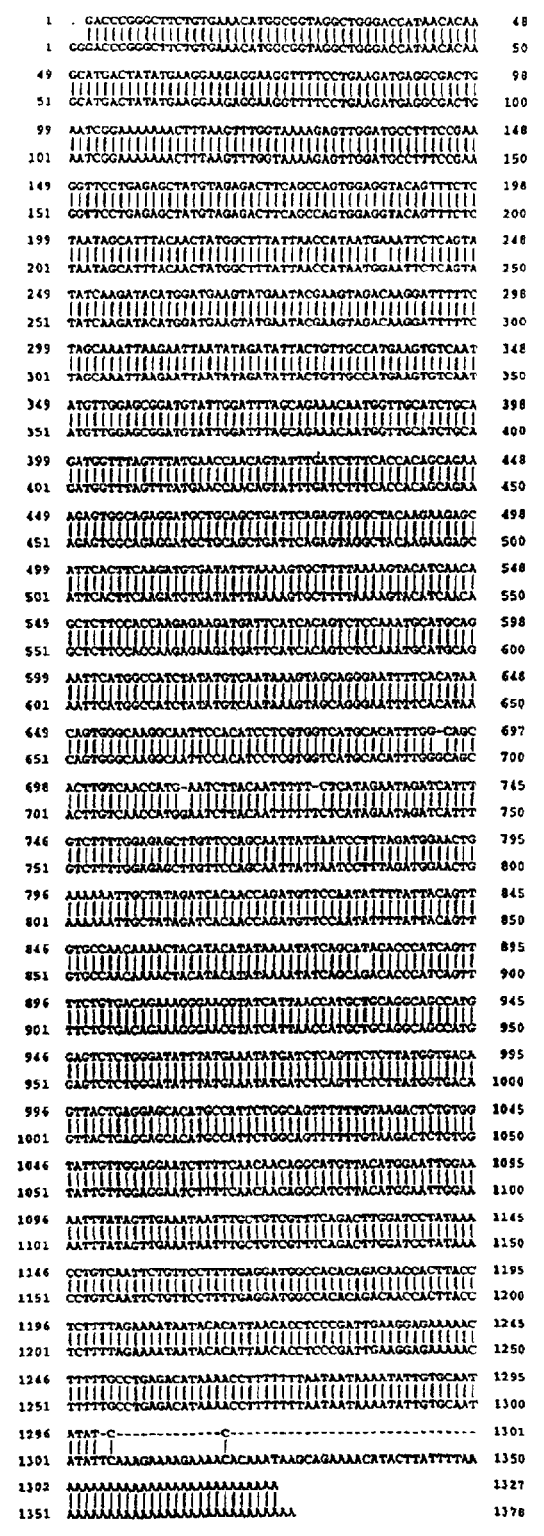

A search of the PTX1 sequence against the GenBank database revealed another cDNA known as CDA14 which encodes a protein with unknown function (Song et al., 2000). Nucleotide sequence homology analysis of PTX1 and CDA14 revealed that they are highly similar. However, there are several significant differences between these two cDNAs (FIG. 6). CDA14 is 2 base pairs (bp) longer than PTX1 at the 5'-end. However, these two extra base pairs are not present in the genomic sequence (discussed in more details below). Its 3'-untranslated region is also 42 bp longer than that of PTX1. This may be due to the utilization of different polyadenylation sites. Multiple polyadenylation sites in mRNA are not unusual and have been reported to be present in other mRNAs such as porcine prohormone convertase PC1/3 (Dai et al., 1995). In the coding region of CDA14, there are three single base insertions at bases 696, 715 and 731, which altered 11 residues of the deduced protein sequence at positions 203–213 (FIG. 7). This change in amino acid sequence may significantly alter the protein's structure and function. There are also two single base differences at bases 239 and 887, which affected single codons each. One possible explanation for these sequence discrepancies is that CDA14 may be a natural mutant, since it was isolated from pheochromocytoma.

A search on the GenBank database also resulted in the identification of the PTX1 gene in a 203 kb fragment of human chromosome 12p (Muzny et al., 2000). This also confirms the chromosomal localization of the PTX1 gene. By comparing this genomic sequence with the cDNA sequence, the location and size of the exons may be determined. The PTX1 gene spans a little over 40 kb, and it contains 14 exons of 41–143 bp and 13 introns of 0.5–9.4 kb (FIG. 9; SEQ ID NOS: 6–31). The TATA or CAAT promoter elements are absent in the 5'-flanking sequence. The genomic sequence also refutes the three single base insertions in the coding region of CDA14 at bases 696, 715 and 731, but confirms the two single base changes in CDA14 at bases 239 and 887 (FIG. 6).

Although loss of chromosome 17 may occur in the early stages of tumorigenesis of the prostate, loss of chromosome 12 (especially 12p) may be associated with more advanced stages (Brothman et al., 1994; Kibel et al., 1998). Using microcell-mediated chromosome transfer, a portion of human chromosome 12 corresponding to 12pter-q13 was shown to possess prostate tumor suppressor activity (Berube et al., 1994). On the other hand, using the same technique, a 70-cM portion of human chromosome 12 has been shown to suppress metastasis, but not tumorignesis (Luu et al., 1998).

Figure 8:
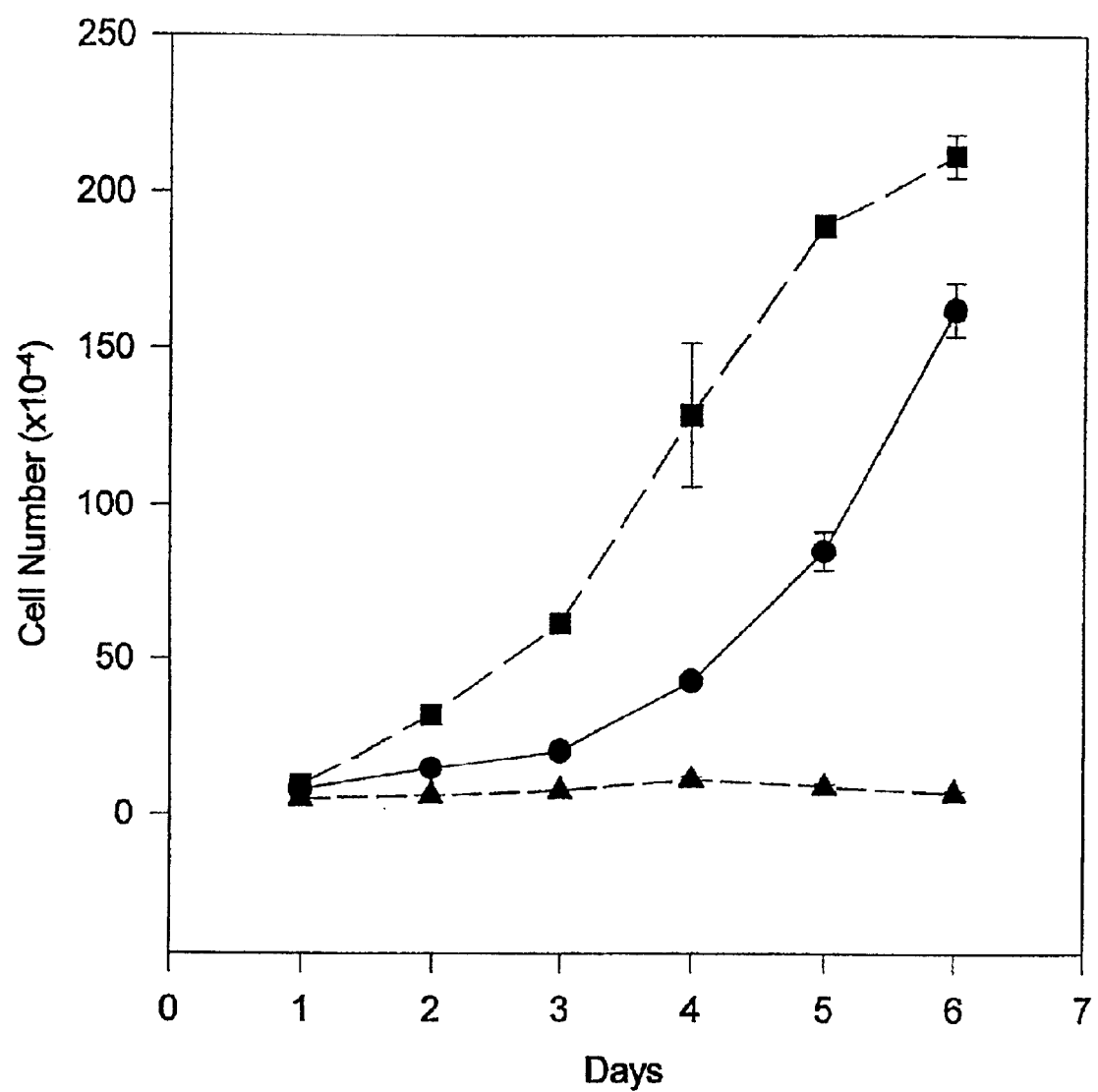
FIG. 8 shows a graph of the in vitro growth curves for PC-3 prostate tumor cells transfected with various expression constructs. Proliferation of cells expressing PTX1 antisense RNA is indicated with squares (■); growth of cells expressing luciferase RNA is indicated with circles (●), and growth of cells expressing PTX1 RNA is indicated by triangles (▲) The results are the averages of three independent experiments.

Additional experiments suggest that PTX1 also suppresses anchorage-independent cell proliferation in human prostate tissue. Expression of PTX1-encoding nucleic acid molecules in the PC-3 prostate tumor cell line resulted in decreased cell proliferation, while expression of antisense PTX1-encoding nucleic acids caused increased cell proliferation (FIG. 8). Thus, when translation of PTX1 is blocked by antisense RNA, cells will grow without control. However, when PTX1 is overexpressed, cell proliferation is arrested. Taken together, these results strongly suggest that PTX1 plays a critical role in suppressing cellular growth and tumor progression in human prostate carcinomas.

REFERENCES

Berube, N. G., Speevak, M. D., and Chevrette, M. (1994). Suppression of tumorigenicity of human prostate cancer cells by introduction of human chromosome del(12)(q13). Cancer Res. 54, 3077–3081.

Brothman, A. R., Watson, M. J., Zhu, X. L., Williams, B. J., and Rohr, L. R. (1994). Evaluation of 20 archival prostate tumor specimens by fluorescence in situ hybridization (FISH). Cancer Genet. Cytogenet. 75, 40–44.

Chomczynski, P., and Sacchi, N. (1987). Single-step method of RNA isolation by acid guanidinium thiocyanate-phenol-chloroform extraction. Anal. Biochem. 162, 156–159.

Dai, G., Smeekens, S. P., Steiner, D. F., McMurtry, J. P., and Kwok, S. C. M. (1995). Characterization of multiple prohormone convertase PC1/3 transcripts in porcine ovary. Biochim. Biophys. Acta 1264, 1–6.

Golemis et al., (1996) Yeast Interaction Trap/Two Hybrid Systems to Identify Interacting Proteins, Unit 20.1.1–20.1.28 in *Current Protocols in Molecular Biology*, eds. Ausubel, F. M. et al., John Wiley & Sons, NY.

Kibel, A. S., Schutte, M., Kern, S. E., Isaacs, W. B., and Bova, G. S. (1998). Identification of 12p as a region of frequent deletion in advanced prostate cancer. Cancer Res. 58, 5652–5655.

Lara, P. N., Jr, Kung, H.-J., Gumerlock, P. H., and Meyers, F. J. (1999). Molecular biology of prostate carcinogenesis. Crit. Rev. Oncol. Hematol. 32, 197–208.

Luu, H. H., Zagaja, G. P., Dubauskas, Z., Chen, S. L., Smith, R. C., Watabe, K., Ichikawa, Y., Ichikawa, T., Davis, E. M., Beau, M. M. L., and Rinker-Schaeffer, C. W. (1998). Identification of a novel metastasis-suppressor region on human chromosome 12. Cancer Res. 58, 3561–3565.

Melchior, F., and Gerace, L. (1995). Mechanisms of nuclear protein import. Curr. Opin. Cell Biol. 7, 310–318.

Muzny, D. M., Adams, C., Bailey, M., Barbaria, J., Blankenburg, K., Bodota, B., Bouck, J., Bowie, S. et al. (2000). *Homo sapiens* 12p BAC RP11-996F15 complete sequence. GenBank database, accession number: AC009318.

Proudfoot, N. J., and Brownlee, G. G. (1976). 3'-Noncoding region sequences in eukaryotic messenger RNA. Nature 263, 211–214.

Reddy, G. K., Gunwar, S., Green, C. B., Fei, D. T. W., Chen, A. B., and Kwok, S. C. M. (1992). Purification and characterization of recombinant porcine prorelaxin expressed in *Escherichia coli*. Arch. Biochem. Biophys. 294, 579–585.

Sciavolino, P. J. and Abate-Shen C. (1998). Molecular biology of prostate development and prostate cancer. Ann. Med. 30, 357–368.

Song, H., Gao, G., Peng, Y., Ren, S., Chen, Z., and Han, Z. (2000). A novel gene expressed in human pheochromocytoma. GenBank database, accession numbers: NM_016570 and AF216751.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for identifying a mutation in a PTX1 nucleic acid sequence in a patient sample, said method comprising:

a) isolating a PTX1 nucleic acid sample from said patient;

b) contacting said PTX1 nucleic acid sample with a nucleic acid sequence of SEQ ID NO: 1, such that DNA duplexes form between sequences of sufficient complementarity;

c) isolating said DNA duplexes if any, and d) assessing said duplexes for mismatched base pairing, wherein said mismatched base pairing is indicative of said mutation in said PTX1 nucleic acid sequence from said patient sample.

2. A method as claimed in claim 1, wherein said mismatched base pairing is due to the presence of a deletion in said nucleic acid from said patient sample.

3. A method as claimed in claim 1, wherein said mismatched base pairing is due to the presence of an insertion in said nucleic acid from said patient sample.

4. A method as claimed in claim 1, wherein said mismatched base pairing is due to the presence of a point mutation.

5. A method of determining loss of a PTX1 encoding nucleic acid molecule in a test sample as a diagnostic indicator of prostate cancer using a diagnostic probe which is a fragment comprising 10–100 contiguous bases from SEQ ID NO: 1 which is capable of specifically hybridizing to the complementary sequence of SEQ ID NO: 1, the method comprising contacting the probe and the test sample under hybridizing conditions and observing whether hybridization takes place, wherein the lack of hybridization serves to identify the loss of said PTX 1 encoding nucleic acid, said loss being correlated with a susceptibility to prostate cancer.

* * * * *

SEQUENCE LISTING

<160> NUMBER OF SEQ ID NOS: 2

<210> SEQ ID NO 1
<211> LENGTH: 1327
<212> TYPE: DNA
<213> ORGANISM: Homo sapiens

<400> SEQUENCE: 1

| | | | | | | |
|---|---|---|---|---|---|---|
| gacccgggct | tctgtgaaac | atggcggtag | gctgggacca | taacacaagc | atgactatat | 60 |
| gaaggaagag | gaaggttttc | ctgaagatga | ggcgactgaa | tcggaaaaaa | actttaagtt | 120 |
| tggtaaaaga | gttggatgcc | tttccgaagg | ttcctgagag | ctatgtagag | acttcagcca | 180 |
| gtggaggtac | agtttctcta | atagcattta | caactatggc | tttattaacc | ataatgaaat | 240 |
| tctcagtata | tcaagataca | tggatgaagt | atgaatacga | agtagacaag | gattttcta | 300 |
| gcaaattaag | aattaatata | gatattactg | ttgccatgaa | gtgtcaatat | gttggagcgg | 360 |
| atgtattgga | tttagcagaa | acaatggttg | catctgcaga | tggtttagtt | tatgaaccaa | 420 |
| cagtatttga | tctttcacca | cagcagaaag | agtggcagag | gatgctgcag | ctgattcaga | 480 |
| gtaggctaca | agaagagcat | tcacttcaag | atgtgatatt | taaaagtgct | tttaaaagta | 540 |
| catcaacagc | tcttccacca | agagaagatg | attcatcaca | gtctccaaat | gcatgcagaa | 600 |
| ttcatggcca | tctatatgtc | aataaagtag | cagggaattt | tcacataaca | gtgggcaagg | 660 |
| caattccaca | tcctcgtggt | catgcacatt | tggcagcact | tgtcaaccat | gaatcttaca | 720 |
| atttttctca | tagaatagat | catttgtctt | ttggagagct | tgttccagca | attattaatc | 780 |
| ctttagatgg | aactgaaaaa | attgctatag | atcacaacca | gatgttccaa | tattttatta | 840 |
| cagttgtgcc | aacaaaacta | catacatata | aaatatcagc | atacacccat | cagttttctg | 900 |
| tgacagaaag | ggaacgtatc | attaaccatg | ctgcaggcag | ccatggagtc | tctgggatat | 960 |
| ttatgaaata | tgatctcagt | tctcttatgg | tgacagttac | tgaggagcac | atgccattct | 1020 |
| ggcagttttt | tgtaagactc | tgtggtattg | ttggaggaat | cttttcaaca | acaggcatgt | 1080 |
| tacatggaat | tggaaaattt | atagttgaaa | taatttgctg | tcgtttcaga | cttggatcct | 1140 |
| ataaacctgt | caattctgtt | ccttttgagg | atggccacac | agacaaccac | ttacctcttt | 1200 |
| tagaaaataa | tacacattaa | cacctcccga | ttgaaggaga | aaaacttttt | gcctgagaca | 1260 |
| taaaaccttt | ttttaataat | aaaatattgt | gcaatatatc | caaaaaaaaa | aaaaaaaaa | 1320 |
| aaaaaaa | | | | | | 1327 |

<210> SEQ ID NO 2
<211> LENGTH: 377
<212> TYPE: PRT
<213> ORGANISM: Homo sapiens

<400> SEQUENCE: 2

Met Arg Arg Leu Asn Arg Lys Lys Thr Leu Ser Leu Val Lys Glu Leu
 1               5                  10                  15

Asp Ala Phe Pro Lys Val Pro Glu Ser Tyr Val Glu Thr Ser Ala Ser
            20                  25                  30

Gly Gly Thr Val Ser Leu Ile Ala Phe Thr Thr Met Ala Leu Leu Thr
        35                  40                  45

-continued

```
Ile Met Lys Phe Ser Val Tyr Gln Asp Thr Trp Met Lys Tyr Glu Tyr
    50              55              60

Glu Val Asp Lys Asp Phe Ser Ser Lys Leu Arg Ile Asn Ile Asp Ile
65              70              75              80

Thr Val Ala Met Lys Cys Gln Tyr Val Gly Ala Asp Val Leu Asp Leu
            85              90              95

Ala Glu Thr Met Val Ala Ser Ala Asp Gly Leu Val Tyr Glu Pro Thr
            100             105             110

Val Phe Asp Leu Ser Pro Gln Gln Lys Glu Trp Gln Arg Met Leu Gln
            115             120             125

Leu Ile Gln Ser Arg Leu Gln Glu Glu His Ser Leu Gln Asp Val Ile
    130             135             140

Phe Lys Ser Ala Phe Lys Ser Thr Ser Thr Ala Leu Pro Pro Arg Glu
145             150             155             160

Asp Asp Ser Ser Gln Ser Pro Asn Ala Cys Arg Ile His Gly His Leu
                165             170             175

Tyr Val Asn Lys Val Ala Gly Asn Phe His Ile Thr Val Gly Lys Ala
            180             185             190

Ile Pro His Pro Arg Gly His Ala His Leu Ala Ala Leu Val Asn His
    195             200             205

Glu Ser Tyr Asn Phe Ser His Arg Ile Asp His Leu Ser Phe Gly Glu
    210             215             220

Leu Val Pro Ala Ile Ile Asn Pro Leu Asp Gly Thr Glu Lys Ile Ala
225             230             235             240

Ile Asp His Asn Gln Met Phe Gln Tyr Phe Ile Thr Val Val Pro Thr
                245             250             255

Lys Leu His Thr Tyr Lys Ile Ser Ala Tyr Thr His Gln Phe Ser Val
            260             265             270

Thr Glu Arg Glu Arg Ile Ile Asn His Ala Ala Gly Ser His Gly Val
            275             280             285

Ser Gly Ile Phe Met Lys Tyr Asp Leu Ser Ser Leu Met Val Thr Val
    290             295             300

Thr Glu Glu His Met Pro Phe Trp Gln Phe Phe Val Arg Leu Cys Gly
305             310             315             320

Ile Val Gly Gly Ile Phe Ser Thr Thr Gly Met Leu His Gly Ile Gly
                325             330             335

Lys Phe Ile Val Glu Ile Ile Cys Cys Arg Phe Arg Leu Gly Ser Tyr
            340             345             350

Lys Pro Val Asn Ser Val Pro Phe Glu Asp Gly His Thr Asp Asn His
            355             360             365

Leu Pro Leu Leu Glu Asn Asn Thr His
    370             375
```